United States Patent
Gou et al.

(10) Patent No.: US 11,193,134 B2
(45) Date of Patent: Dec. 7, 2021

(54) METHODS AND COMPOSITIONS FOR REGULATION OF PLANT GROWTH

(71) Applicant: NOBLE RESEARCH INSTITUTE, LLC, Ardmore, OK (US)

(72) Inventors: Jiqing Gou, Ardmore, OK (US); Zeng-Yu Wang, Ardmore, OK (US)

(*) Notice: Subject to any disclaimer, the term of this patent is extended or adjusted under 35 U.S.C. 154(b) by 0 days.

(21) Appl. No.: 16/029,367

(22) Filed: Jul. 6, 2018

(65) Prior Publication Data

US 2019/0177740 A1 Jun. 13, 2019

Related U.S. Application Data

(60) Provisional application No. 62/530,134, filed on Jul. 8, 2017.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8218* (2013.01)

(58) Field of Classification Search
None
See application file for complete search history.

(56) References Cited

U.S. PATENT DOCUMENTS

2002/0069433 A1* 6/2002 Schmidt .................. C12N 9/12
800/298

OTHER PUBLICATIONS

Schwab et al. Specific effects of microRNAs on the plant transcriptome. Dev Cell. Apr. 2005;8(4):517-27. (Year: 2005).*
Aung et al. MicroRNA156 as a promising tool for alfalfa improvement. Plant Biotechnol J. Aug. 2015;13(6):779-90. Epub Dec. 23, 2014. (Year: 2015).*
Gao et al. Comparative transcriptome investigation of global gene expression changes caused by miR156 overexpression in Medicago sativa. BMC Genomics. Aug. 19, 2016;17(1):658. (Year: 2016).*
Farrell. The Regulation of Gene Expression in Plants and Animals. Chapter 1 pp. 1-38 In Regulation of Gene Expression in Plants, Edited by Carole L. Bassett., 2007, Springer. (Year: 2007).*
Si et al. OsSPL13 controls grain size in cultivated rice. Nat. Genet. Apr. 2016;48(4):447-56. Epub Mar. 7, 2016. (Year: 2016).*
Preston et al. Squamosa-promoter binding protein 1 initiates flowering in Antirrhinum majus through the activation of meristem identity genes. Plant J. 2010; 22(7):2322-35. (Year: 2010).*

Chuck, et al., "Overexpression of the maize Corngrass1 Micro-RNA Prevents Flowering, Improves Digestibility, and Increases Starch Content of Switchgrass," Proceedings of the National Academy of Sciences of the United States of America vol. 108, p. 17550, (2011).
Fu, et al., "Overexpression of miR156 in Switchgrass (*Panicum virgatum* L.) Results in Various Morphological Alterations and Leads to Improved Biomass Production," Journal of Plant Biotechnology 10:443-452 (2012).
Gallavotti, et al., "The Relationship Between Auxin Transport and Maize Branching," Plant Physiology 147:1913-1923 (2008).
Jiao, et al., "Regulation of OsSPL14 by OsmiR156 Defines Ideal Plant Architecture in Rice," Nature Genetics 42:541-544(2010).
Mauro-Herrera and Doust, "Development and Genetic Control of Plant Architecture and Biomass in the Panicold Grass," Setaria. PLoS One 11, e0151346 (2016).
Miura, et al., "OsSPL14 Promotes Panicle Branching and Higher Grain Productivity In Rice," Nature Genetics 42:545-549 (2010).
Oikawa and Kyozuka, "Two-Step Regulation of LAX PANICLE1 Protein Accumulation in Axillary Meristem Formation in Rice," Plant Cell 21:1095-1108 (2009).
Reinhart, et al., "MicroRNAs in Plants," Genes Dev. 16:1616-1626 (2002).
Schwab, et al., "Specific Effects of MicroRNAs on the plant Transcriptome," Developmental Cell 8:517-527 (2005).
Si, et al., "OsSPLI3 Controls Grain Size in Cultivated Rice," Nat Genet 48:447-456 (2016).
Tatematsu, et al., "A Molecular Mechanism That Confines the Activity Pattern of miR165 in Arabidopsis leaf primordia," Plant Journal 82:596-608 (2015).
Tian, et al., "An Organ Boundary-enriched Gene Regulatory Network Uncovers Regulatory Hierarchies Underlying Axillary Meristem Initiation," Mol Syst Biol 10:755 (2014).
Wang, et al., "miR156-reguiated SPL Transcription Factors Define an Endogenous Flowering Pathway in *Arabidopsis thaliana*," Cell 138:738-749 (2009).
Wang, et al., "The OsSPL16~GW7 Regulatory Module Determines Grain Shape and Simultaneously Improves Rice Meld and Grain Quality," Nature Genetics 47:949-954 (2015).
Xie, et al., "Genomic Organization, Differential Expression, and Interaction of SQUAMOSA Promoter-binding-like Transcription Factors and MicroRNA 156 in Rice," Plant Physiology 142:280-293 (2006).
Xing, et al., "miR156-Targeted and Nontargeted SBP-Box Transcription Factors Act in Concert to Secure Male Fertility in Arabidopsis," Plant Cell 22:3935-3950 (2010).
Yamaguchi, et al., "The MicroRNA-regulated SBP-Box Transcription Factor SPL3 Is a Direct Upstream Activator of Leafy, Fruitfull, and APETALA1," Dev Cell 17:268-278 (2009).

* cited by examiner

*Primary Examiner* — Cynthia E Collins
(74) *Attorney, Agent, or Firm* — Dentons US LLP

(57) ABSTRACT

The present invention provides methods for regulating plant architecture, improving biomass yield or regrowth after cutting through down-regulation of SPL4 gene function. Also provided are transgenic plants with improved biomass yield or regrowth after cutting produced by such methods.

19 Claims, 26 Drawing Sheets

Specification includes a Sequence Listing.

Bright field

YFP inflorescence

FIG. 24

METHODS AND COMPOSITIONS FOR REGULATION OF PLANT GROWTH

REFERENCE TO RELATED APPLICATIONS

This application claims the benefit of U.S. Provisional Patent Application Ser. No. 62/530,134, filed Jul. 8, 2017, which is herein incorporated by reference in its entirety.

INCORPORATION OF SEQUENCE LISTING

The sequence listing that is contained in the file named "NBLE095US-substitute ST25.txt," which is 24 kilobytes as measured in Microsoft Windows operating system and was created on Feb. 27, 2018, is filed electronically herewith and incorporated herein by reference.

FIELD OF THE INVENTION

The present invention relates generally to the field of molecular biology. More specifically, the invention relates to genes involved in regulation of axillary bud formation and shoot architecture, and methods of use thereof.

BACKGROUND OF THE INVENTION

Branch development (branching) determines shoot architecture and biomass yield. Axillary buds are the sole originators of tillers and branches (Domagalska and Leyser, Nat. Rev. Mol. Cell Biol. 12:211-221, 2011). Grasses have two types of buds: basal axillary buds (basal buds) that arise from the base of the main shoot and eventually become tillers/branches, and aerial axillary buds (aerial buds) that arise from elongated internodes and ultimately become aerial branches (Domagalska and Leyser, 2011; Oikawa and Kyozuka, Plant Cell 21:1095-1108, 2009). Axillary bud development has two stages—formation (initiation) and outgrowth (Kebrom, et al., Trends Plant Sci. 18:41-48, 2013). In the last two decades, axillary bud outgrowth has been extensively studied and the regulatory mechanisms have been well elucidated (Domagalska and Leyser, 2011; Kebrom, et al., 2013; Wang and Li, Curr. Opin. Plant Biol. 14:94-99, 2011). The common mechanisms of bud outgrowth are conserved between monocots and eudicots (Kebrom, et al., 2013; McSteen, Plant Physiol. 149:46-55, 2009). In contrast, our understanding of bud initiation remains rudimentary (Tian, et al., Mol. Syst. Biol. 10:755, 2014; Tanaka, et al., Plant Cell 27:1173-1184, 2015). To date, two classes of genes have been identified in regulating bud initiation in various species. The first class contains MOC1 (and its orthologs, such as LAS in *Arabidopsis*) (Greb, et al., Genes Dev. 17:1175-1187, 2003; Li, et al., Nature 422:618-621, 2003) and YUCs (Gallavotti, et al., Proc. Natl. Acad. Sci. USA 105:15196-15201, 2008; Cheng, et al., Genes Dev. 20:1790-1799, 2006). The second class includes LAX1 and its orthologs (such as BA1 in maize, ROX in *Arabidopsis*) (Komatsu, et al., Proc. Natl. Acad. Sci. USA 100:11765-11770, 2003; Gallavotti, et al., Nature 432:630-635, 2004) and PIN1 orthologs (Michniewicz, et al., Cell 130:1044-1056, 2007); these genes are related to auxin transport and redistribution (McSteen, 2009). In rice, TAB1 was found to be required for axillary bud formation and to act downstream of MOC1 or LAX1 (Tanaka, et al., 2015). However, all of these molecular mechanism studies focused on basal bud formation and did not explore the subject of aerial buds. Basal buds normally continue to develop across initiation and outgrowth stages. The development of aerial buds varies in different species. For instance, aerial buds may continue to develop to form aerial branches in *Brachypodium* and many panicoid grasses (Doust, Ann. Bot. 100:941-950, 2007), or may arrest at an early stage and remain dormant due to apical dominance in wheat, barley and rice (Kebrom, et al., 2013). However, certain conditions such as long-term heat stress could induce dormant aerial buds to enter the outgrowth stage and form aerial branches in rice. The genetic control of aerial bud formation is largely unknown, although some quantitative trait loci (QTL) for aerial branching have been identified (Mauro-Herrera and Doust, PLoS One 11:e0151346, 2016).

microRNA156 (miR156) is one of the most evolutionarily conserved microRNAs in plants and has broad functions including regulation of stem, flower and leaf development in various species (Schwab, et al., Dev. Cell 8:517-527, 2005; Xie, et al., Plant Physiol. 142:280-293, 2006; Fu, et al., Plant Biotechnol. J. 10:443-452, 2012; Chuck, et al., Proc. Natl. Acad. Sci. USA 108:17550-17555, 2011; Tatematsu, et al., Plant J. 82:596-608, 2015). Overexpression of miR156 dramatically improved tillering in rice (Xie, et al., 2006) and switchgrass (Fu, et al., 2012; Chuck, et al., 2011). miR156 targets SQUAMOSA PROMOTER BINDING PROTEIN LIKE (SPL) transcription factor genes (Reinhart, et al., Genes Dev. 16:1616-1626, 2002; Xing, et al., Plant Cell 22:3935-3950, 2010). Higher levels of OsSPL14 suppressed tillering while promoting panicle branching in rice (Jiao, et al., Nat. Genetics 42:541-544, 2010; Miura, et al., Nat. Genetics 42:545-549, 2010).

Enhancement of biomass productivity of important agricultural and biofuel crops would represent a significant advancement in the art. Accordingly, methods capable of regulating axillary bud formation and shoot architecture through gene regulation are described.

SUMMARY OF THE INVENTION

In one aspect the invention provides a plant comprising up- or down-regulated SPL4 gene function, wherein the plant exhibits an enhanced agronomic property as a result of up- or down-regulated SPL4 gene function. In certain embodiments, the plant comprises a first DNA molecule capable of expressing a nucleic acid sequence complementary to all or a portion of a SPL4 messenger RNA (mRNA); or b) a second DNA molecule capable of increased expression of miR156 in said plant relative to a plant lacking said DNA molecule. In other embodiments, the plant comprises a DNA molecule complementary to all or a portion of a SPL4 mRNA, wherein the DNA molecule down-regulates the function of the SPL4 gene relative to a plant lacking said DNA molecule. The plant may also comprise a mutation in said SPL4 gene relative to a wild-type plant of the same species, including wherein the mutated genomic SPL4 gene comprises a deletion, a point mutation or an insertion in said SPL4 gene. A mutated genomic SPL4 gene can be produced by irradiation, T-DNA insertion, transposon insertion or chemical mutagenesis, for example. A plant of the invention may also comprise all or a portion of the sequences described herein, including all or a portion of a nucleic acid sequence selected from the group consisting of SEQ ID NO:1, 3, 4, 6, 8, 9, and 11 or a coding sequence for a protein with an amino acid sequence selected from the group consisting of SEQ ID NO:2, 5, 7, and 10, wherein transcription of said all or a portion of said nucleic acid sequence in the plant down-regulates the function of said SPL4 gene.

In further embodiments of the invention, a plant provided herein may be a monocotyledonous plant including, but not limited to corn, rice, wheat, sorghum, barley, oat, switchgrass, and turfgrass. A plant may also be aa dicotyledonous plant, including but not limited to, cotton, soybean, rapeseed, sunflower, tobacco, sugarbeet, alfalfa and a legume. In specific further embodiments, a plant of the invention may comprise an enhanced agronomic property selected from the group consisting of increased branching, enhanced regrowth after cutting, and increased biomass yield compared to a plant in which the SPL4 gene is not down-regulated. A plant of the invention may also comprise a first or second DNA molecule operably linked to a developmentally-regulated, organelle-specific, inducible, tissue-specific, constitutive, cell specific, seed specific, or germination-specific promoter. In one embodiment, a plant is an R0 transgenic plant, and in others it is defined as a progeny plant of any generation of an R0 transgenic plant, wherein the transgenic plant has inherited said DNA molecule. Also provided by the invention are a seed that produces a plant described herein, and DNA-containing plant parts, including a protoplast, cell, meristem, root, leaf, node, pistil, anther, flower, seed, embryo, stalk or petiole.

In another aspect, the invention provides a method of increasing biomass yield or regrowth after cutting in a plant, comprising down-regulating SPL4 gene function in said plant, wherein the biomass yield or regrowth after cutting is increased as compared to a plant that lacks said down-regulating. In the method the plant may be a monocotyledonous or dicotyledonous plant.

In yet another aspect, the invention provides a method of producing a plant comprising increased biomass yield or regrowth after cutting, the method comprising: (a) obtaining a plant comprising down-regulation of SPL4 gene function, wherein the biomass yield or regrowth after cutting is increased as compared to a plant that lacks said down regulation; (b) growing said plant; (c) crossing said plant with itself or another distinct plant to produce progeny plants; and (d) selecting a progeny plant comprising down-regulation of SPL4 gene function, wherein said progeny plant comprises increased biomass yield or regrowth after cutting as compared to a plant that lacks said down-regulation.

In still yet another aspect, the invention provides a transgenic plant comprising a recombinant DNA molecule, wherein the recombinant DNA molecule down-regulates SPL4 gene function, wherein said down-regulation increases biomass yield or regrowth after cutting. The plant may be, for example, a dicotyledonous or monocotyledonous plant, including switchgrass, alfalfa, or a legume. The plant may be an R0 transgenic plant as well as a progeny plant of any generation of an R0 transgenic plant, wherein the transgenic plant has inherited the recombinant DNA molecule from the R0 transgenic plant.

BRIEF DESCRIPTION OF THE DRAWINGS

FIG. 1 panels a-c show nodal segments harvested from switchgrass genotypes ST2 (FIG. 1 panel a), NFCX1 (FIG. 1 panel b) and an overexpressor of miR156 in NFCX1 background (FIG. 1 panel c) for node culture. FIG. 1 panels d-f show shoot formation from the nodal segments after 12 days in culture. Shoots emerged from ST2 (FIG. 1 panel d) and miR156-NFCX1 (FIG. 1 panel f), but no shoots were formed from NFCX1 (FIG. 1 panel e). FIG. 1 panels g-i show formation of aerial axillary bud. Buds were formed in ST2 (FIG. 1 panel g) and miR156-NFCX1 (FIG. 1 panel i) but no aerial axillary buds were found in NFCX1 (FIG. 1 panel h). Arrows indicate the aerial axillary buds.

FIG. 2 panel a shows developmental status of aerial axillary buds in different miR156 plants. FIG. 2 panel b shows relative levels of miR156. Values represent mean±S.D. of three replicates.

FIG. 4 panel a shows SEM observation of aerial axillary bud development in SPL4Ri plants. FIG. 4 panel b shows expression levels of PvSPL4s. Values represent mean±S.D. of three replicates.

FIG. 5 panel a shows down-regulation of PvSPL4 in WT-NFCX1 significantly increased tiller number and biomass yield, especially in secondary harvests after cutting. $1^{st}$ H, the first harvest; $2^{nd}$ H, the second harvest. Values represent mean±S.D. of three replicates. FIG. 5 panel b shows down-regulation of PvSPL4 accelerated plant regrowth after cutting. FIG. 5 panel c shows new stem (branch, red arrow) produced from the outgrowth of the aerial axillary bud in SPL4Ri plant. M, main stem; T, tiller. FIG. 5 panels d and e show enlargements of the boxed regions in FIG. 5 panel c. Arrows indicate more basal axillary buds formed in the SPL4Ri plant (FIG. 5 panel e).

FIG. 1 panels a-c show knock-out MtSPL4 significantly improved branching in the spl4 mutant. FIG. 1 panels a-c show 7-week-old plants. FIG. 1 panel D shows both fresh and dried biomass significantly increased in spl4 mutants. FIG. 6 panels e-g show overexpression of MtSPL4 inhibited branching and altered shoot architecture. FIG. 6 panels e-g show 11-week-old plants. Values represent mean±S.D. of three replicates.

FIG. 8 panels a-c show nodal segments excised from various nodes of three genotypes. FIG. 8 panels d-f show shoot formation from the nodal segments after 6 days culture. New shoots emerged in both ST2 (FIG. 8 panel d) and AP13 (FIG. 8 panel e) while NFCX1 failed to form any shoots and all segments died (FIG. 8 panel f).

FIG. 10 panel a shows a switchgrass tiller (genotype ST2) shows different nodes after removing leaf sheath. FIG. 10 panel b shows aerial axillary bud formed in the elongated internode. FIG. 10 panel c shows SEM of a cross section of an aerial bud (FIG. 10 panel b, cut at the dashed line). FIG. 10 panel d shows enlargements of the regions framed in white in FIG. 10 panel c. FIG. 10 panel e shows basal axillary bud formed in the non-elongated internode. FIG. 10 panel f shows SEM of a cross-section of a basal bud (FIG. 10 panel e, cut at the dashed line). FIG. 10 panel g shows enlargements of the regions framed in white in FIG. 10 panel f. AM, apical meristem; pp, prophyll; fl, foliage leaf; LP, leaf primordia.

FIG. 14 panel a shows tiller numbers of 4 different wild-type genotypes and 4 transgenic lines. FIG. 14 panel b shows relative expression levels of PvSPL4 and 5. FIG. 14 panels c and d show correlation analysis ($R^2$) of tiller development and expression levels of PvSPL4 (FIG. 14 panel c) and 5 (FIG. 14 panel d). Values represent mean±S.D. of three replicates.

FIG. 19 panels b and e show upper cross-sections of aerial axillary buds of PvSPL4RNAi construct (FIG. 19 panel b) and wild-type genotype ST2 (FIG. 19 panel e). Arrows point the tips of AM. FIG. 19 panel c and FIG. 19 panel f show lower cross-sections of aerial axillary buds of PvSPL4RNAi construct (FIG. 19 panel c) and wild-type genotype ST2 (FIG. 19 panel f). AM, apical meristem; pp, prophyll; fl, foliage leaf.

FIG. 21 panel a shows both LAX1 and MOC1 are significantly up-regulated in SPL4Ri plants. FIG. 21 panel b shows the level of IAA is significantly decreased in node axillary meristems but increased in the surrounding tissues of the meristems (surrounding tissues) in transgenic plants. Values represent mean±S.D. of five replicates. $p<0.01$, *$p<0.001$.

FIG. 24—Shows amino acid alignment of PvSPL4 (SEQ ID NO:18) and MtSPL4 (Medtr8g005960, SEQ ID NO:19). The result indicates that the two genes are highly similar, especially in the conserved functional SBP domain (SQUAMOSA-promoter binding protein) that is highlighted in yellow.

FIG. 25 panel a shows Tnt1 retrotransposon insertion sites of three MtSPL4 (Medtr8g005960) mutants. FIG. 25 panel b shows four-week-old plants showing similar phenotypes of increased branching in the mutants. FIG. 25 panel c shows semiquantitative PCR indicating that MtSPL4 expression is abolished in the spl4 mutants.

FIG. 26 panel a shows MtSPL4 expression levels in different transgenic plants. FIG. 26 panel b shows overexpression of MtSPL4 inhibited branch formation and decreased biomass yield.

BRIEF DESCRIPTION OF THE SEQUENCES

SEQ ID NO:1—*Medicago truncatula* squamosa promoter binding protein-like 4 (SPL4) coding sequence.
SEQ ID NO:2—*Medicago truncatula* squamosa promoter binding protein-like 4 protein sequence.
SEQ ID NO:3—*Medicago truncatula* squamosa promoter binding protein-like 4 upstream sequence.

SEQ ID NO:4—*Arabidopsis thaliana* squamosa promoter binding protein-like 4 coding sequence.

SEQ ID NO:5—*Arabidopsis thaliana* squamosa promoter binding protein-like 4 protein sequence.

SEQ ID NO:6—*Glycine max* squamosa promoter binding protein-like 4 coding sequence.

SEQ ID NO:7—*Glycine max* squamosa promoter binding protein-like 4 protein sequence.

SEQ ID NO:8—*Glycine max* squamosa promoter binding protein-like 4 upstream sequence.

SEQ ID NO:9—*Phaseolus vulgaris* squamosa promoter binding protein-like 4 coding sequence.

SEQ ID NO:10—*Phaseolus vulgaris* squamosa promoter binding protein-like 4 protein sequence.

SEQ ID NO:11—*Phaseolus vulgaris* squamosa promoter binding protein-like 4 upstream sequence.

SEQ ID NO:12—*Phaseolus vulgaris* squamosa promoter binding protein-like 2 (SPL2) nucleotide sequence shown in FIG. 11A.

SEQ ID NO:13—*Phaseolus vulgaris* squamosa promoter binding protein-like 4 (SPL4) nucleotide sequence shown in FIG. 11B.

SEQ ID NO:14—*Phaseolus vulgaris* squamosa promoter binding protein-like 5 (SPL5) nucleotide sequence shown in FIG. 11C.

SEQ ID NO:15—miR156 RNA sequence.

Figure 15:
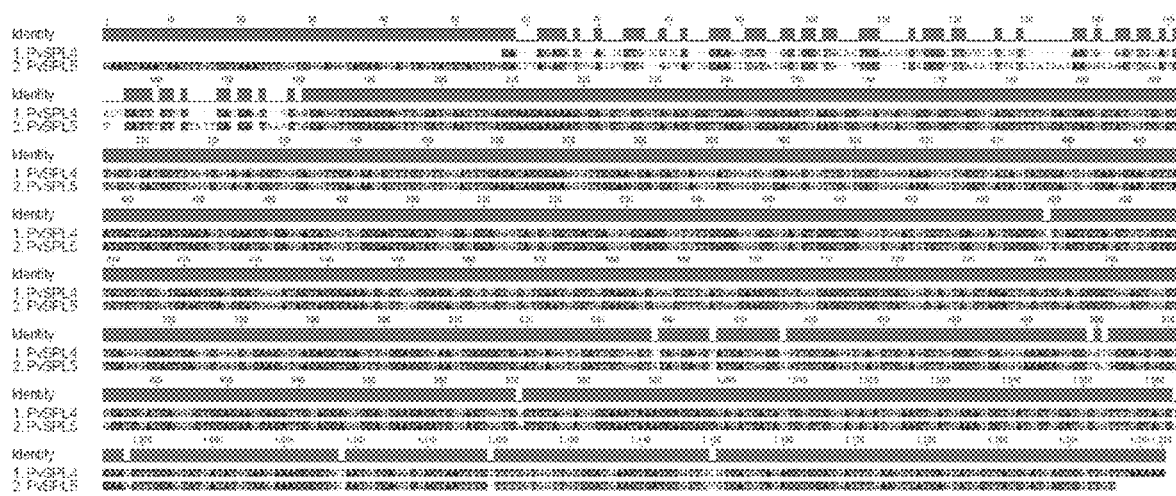
FIG. 15—Shows sequence analysis of PvSPL4 (SEQ ID NO:16) and PvSPL5 (SEQ ID NO:17). Sequence analysis indicates that PvSPL4 and 5 are highly similar in the coding region but different in the 5' UTR.

SEQ ID NO:16—*Phaseolus vulgaris* squamosa promoter binding protein-like 4 (SPL4) nucleotide sequence shown in FIG. 15.

SEQ ID NO:17—*Phaseolus vulgaris* squamosa promoter binding protein-like 5 (SPL5) nucleotide sequence shown in FIG. 15.

Figure 24:
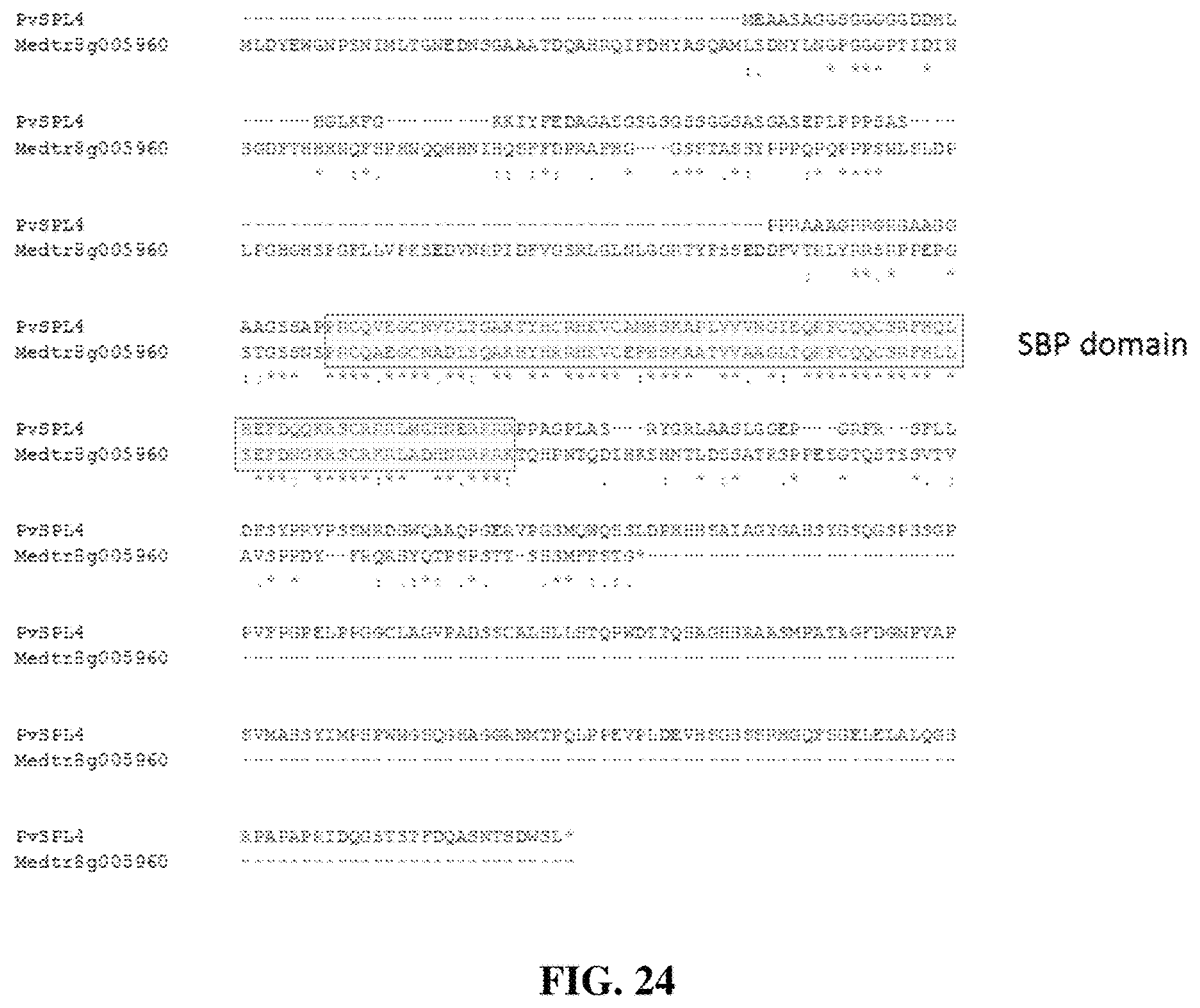

SEQ ID NO:18—*Phaseolus vulgaris* squamosa promoter binding protein-like 4 (SPL4) protein sequence shown in FIG. 24.

SEQ ID NO:19—*Medicago truncatula* squamosa promoter binding protein-like 4 (SPL4) protein sequence shown in FIG. 24.

DETAILED DESCRIPTION OF THE INVENTION

The present invention provides a method of altering shoot architecture, improving biomass yield and accelerated regrowth after cutting in plants, including switchgrass, alfalfa and legumes, by overexpression of miR156 or inhibiting expression of a SPL4 gene. Plants of the present invention that exhibit increased expression of miR156 or altered expression of a SPL4 gene demonstrate beneficial traits including increased aerial bud formation, increase of basal bud formation, increased branching, enhanced regrowth after cutting and improved biomass yield compared to plants that lack said increased expression of miR156 or decreased expression of a SPL4 gene.

Switchgrass (*Panicum virgatum*) is a C4 perennial tetraploid bunchgrass that has been developed into a dedicated biofuel crop because of its high biomass yield, low agricultural input and the ability to grow in marginal lands (Schmer, et al., Proc. Natl. Acad. Sci. USA 105:464-469, 2008; Hardin, et al., Bioenergy Research 6:755-762, 2013). In the present disclosure, it is shown that some switchgrass genotypes are completely devoid of aerial buds. Detailed characterization of such genotypes revealed that axillary bud formation is directly regulated by miR156 and PvSPL4. Unlike previously characterized genes, the miR156-SPL4 module specifically controls the formation of aerial buds but partially regulates basal bud development. These results also indicate that this module is conserved in the model legume *Medicago truncatula*. Furthermore, genetic manipulation of the module led to altered shoot architecture, improved biomass yield and accelerated regrowth after cutting in both switchgrass and legume, thus offering great potential for enhancing agricultural productivity.

The architecture of a plant affects its ability to compete for resources and its agronomic performance. The complexity and adaptability of plant architecture depends on the establishment of new axes of growth through the production of secondary axillary meristems (McSteen and Leyser, Ann. Rev. Plant Biol. 56:353-374, 2005). Tillering is a common trait that determines architecture in major monocot crops (e.g., wheat, rice, barley). A number of genes that control basal bud and tiller development have been identified (Kebrom, et al., 2013; Wang and Li, 2011; Greb, et al., 2003; Li, et al., 2003). Conversely, aerial buds largely remain dormant in domesticated species and are not obviously noticeable. In certain less-domesticated species, aerial buds continue to develop and contribute to the formation of plant architecture. Very limited information is available on the genetic regulation of aerial bud formation in monocots. A recent mapping study using domesticated foxtail millet and its wild relative, green millet, identified 9 quantitative trait loci (QTLs) explaining 42.4% of the phenotypic variance of aerial branching (Mauro-Herrera and Doust, PLoS One 11:e0151346, 2016). The study also showed that aerial branching QTLs often overlap with tillering QTLs, although some aerial branching QTL regions are independent. Co-regulation of tillering and panicle branching has been reported in rice, such as MOC1 and LAX1, both genes are involved in the formation of tillers and panicles (Kebrom, et al., 2013; Wang and Li, 2011; McSteen, 2009). On the other hand, most genes regulate only one process. For example, OsCKX2 and SP1 regulate panicle branching but have no effects on tillering (Ashikari, et al., Science 309:741-745, 2005; Luo, et al., Plant Cell Physiol. 53:1793-1801, 2012; Li, et al., Plant J. 58:592-605, 2009). In the case of OsSPL14, this gene regulates tillering and panicle branching in an opposite manner (Jiao. et al., Nat. Genet. 42:541, 2010; Miura, et al., Nat. Genet. 42:545, 2010). As mentioned above, some genotypes, including NFCX1, have only basal buds and no aerial buds. The present disclosure shows that overexpression of miR156 induced aerial bud formation in NFCX1. Further investigation revealed that PvSPL4 is a specific target of miR156 and negatively regulates axillary bud development. Knockdown of PvSPL4 significantly promoted aerial bud formation along with an increase of basal buds. Consistently, overexpression of PvSPL4 dramatically suppressed axillary bud development. These results showed that, in contrast to all known genes that act as activators of basal bud formation, PvSPL4 is a suppressor, and the miR156-SPL4 module predominantly controls aerial bud formation but only partially regulates basal bud formation.

Eleven miR156-targeted SPLs have been identified in rice (Mauro-Herrera and Doust, PLoS One 11:e0151346, 2016), *Arabidopsis* (Hardin, et al., Bioenergy Research 6:755-762, 2013) and *M. truncatula*. The SPL family is highly conserved across monocots and eudicots (Wang, et al., Cell 138:738-749, 2009), but each individual member may function divergently in regulation of various processes. For example, AtSPL3 promotes floral transition via directly activating FRUITFULL, LEAFY and APETALA1 (Yamaguchi, et al., Dev. Cell 17:268-278, 2009); AtSPL9 controls the initiation of axillary meristems in cauline leaf axils via directly suppressing LAS (Tian, et al., 2014); OsSPL13 and OsSPL16 regulate grain size and shape (Wang, et al., Nat.

Genet. 47:944-948, 2015; Si, et al., Nat. Genet. 48:447-456, 2016); and OsSPL14 promotes panicle branching (Jiao. et al., 2010; Miura, et al., 2010). Different from other SPLs, the PvSPL4 reported here not only inhibits the development of aerial branches but also partially suppresses tillering capacity. Furthermore, down-regulation of PvSPL4 alters shoot architecture, improves regrowth and biomass yield in switchgrass and a legume species.

In one embodiment, a plant in accordance with the invention having increased aerial bud formation, increased branching, improved biomass yield and/or accelerated regrowth after cutting can comprise down-regulation of an endogenous SPL4 gene sequence, or overexpression of a miR156 sequence. In another embodiment, a plant with increased biomass yield or regrowth after cutting can comprise down-regulation of an endogenous SPL4 gene sequence, or overexpression of a miR156 sequence. In other embodiments, the invention provides primers which may be useful for detection or amplification of a sequence as described herein. In another embodiment, such primers may be useful for detecting the presence of absence of a gene or sequence of the invention. In accordance with the invention, nucleic acid and/or protein sequences may share sequence identity at the nucleic acid or amino acid level. For example, such sequences may share 100%, 99%, 98%, 97%, 96%, 95%, 94%, 93%, 92%, 91%, 90%, 89%, 88%, 87%, 86%, 85%, 84%, 83%, 82%, 81%, 80% sequence identity, or the like. When a sequence is referred to in the current disclosure, this includes any of the nucleic acid and protein sequences shown described herein, including SEQ ID NOs:1-11.

In some embodiments, a plant according to the invention may be a monocotyledonous plant or a dicotyledonous plant. In other embodiments, the plant may be a forage plant, a biofuel crop, a cereal crop, or an industrial plant, or a legume. In one embodiment, a forage plant may include, but is not limited to, a forage soybean, alfalfa, clover, Bahia grass, Bermuda grass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, reed canarygrass plant, switchgrass (*Panicum virgatum*), or the like. In certain other embodiments, the plant may be a biofuel crop including, but not limited to, switchgrass (*Panicum virgatum*), giant reed (*Arundo donax*), reed canarygrass (*Phalaris arundinacea*), *Miscanthus* x *giganteus*, *Miscanthus* sp., *sericea lespedeza* (*Lespedeza cuneata*), corn, sugarcane, sorghum, millet, ryegrass (*Lolium multiflorum*, *Lolium* sp.), timothy, *Kochia* (*Kochia scoparia*), soybeans, alfalfa, tomato, clover, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass or poplar. Cereal crops for use according to the present invention include, but are not limited to, maize, rice, wheat, barley, sorghum, millet, oat, rye, triticle, buckwheat, fonio, and quinoa.

I. Nucleic Acids, Polypeptides, and Plant Transformation Constructs

Certain embodiments of the current invention concern recombinant nucleic acid sequences comprising all or a portion of a SPL4 coding sequence, including but not limited to all or a portion of a nucleic acid sequence selected from the group consisting of SEQ ID NO:1, 3, 4, 6, 8, 9, and 11 or of a coding sequence for a protein with an amino acid sequence selected from the group consisting of SEQ ID NO:2, 5, 7, and 10. The invention also provides sequences complementary to such sequences. Also provided are primers for detecting or amplifying a sequence in accordance with the invention. Complements to any nucleic acid sequences described herein are also provided.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by methods well-known to those of ordinary skill in the art. Computer programs that can be used to determine "identity" between two sequences may include, but are in no way limited to, GCG (Devereux, et al., Nucleic Acids Res. 11:387-395, 1984); the suite of five BLAST programs, three designed for nucleotide sequences queries (BLASTN, BLASTX, and TBLASTX) and two designed for protein sequence queries (BLASTP and TBLASTN) (Altschul, et al., J. Mol. Biol. 215:403-410, 1990; Coulson, Trends Biotechnol. 12:76-80, 1994). The BLAST programs are publicly available from NCBI and other sources (NCBI NLM NIH, Bethesda, Md. 20894). The well-known Smith Waterman algorithm can also be used to determine identity.

Parameters for polypeptide sequence comparison include the following: Algorithm: Needleman and Wunsch (J. Mol. Biol. 48:443-453, 1970); Comparison matrix: BLOSUM62 from Hentikoff and Hentikoff (Proc. Natl. Acad. Sci. USA 89:10915-10919, 1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison are known in the art and may include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes," or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well-known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The nucleic acids provided herein may be from any source, e.g., identified as naturally occurring in a plant, or synthesized, e.g., by mutagenesis of a sequence set forth herein. In an embodiment, the naturally occurring sequence may be from any plant. In certain embodiments, the plant can be a monocotyledonous plant or a dicotyledonous plant.

Coding sequences, such as a SPL4 coding sequence, or portions or complements thereof, may be provided in a recombinant vector or construct operably linked to a heterologous promoter functional in plants, in either sense or antisense orientation. In other embodiments, plants and plant cells transformed with the sequences may be provided. The construction of vectors which may be employed in conjunction with plant transformation techniques using these or other sequences according to the invention will be known to those of skill of the art in light of the present disclosure (e.g., Sambrook et al., In: Molecular Cloning-A Laboratory Manual (second edition), Cold Spring Harbour Laboratory Press, 1989). The techniques of the current invention are thus not limited to any particular nucleic acid sequences.

The choice of any additional elements used in conjunction with the SPL4 sequences may depend on the purpose of the transformation. One of the major purposes of transformation of crop plants is to add commercially desirable, agronomically important traits to the plant, as described herein. Such traits may include, but are not limited to increased branching, increased aerial bud formation, increased biomass yield, increased regrowth after cutting, and the like.

Vectors or constructs used for plant transformation may include, for example, plasmids, cosmids, YACs (yeast artificial chromosomes), BACs (bacterial artificial chromosomes) or any other suitable cloning system known in the art, as well as fragments of DNA therefrom. Thus, when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. In an embodiment, introduction of such a construct into a plant may result in increased expression of a particular gene in the plant. In another embodiment, introduction of such a construct may result in reduction or elimination of expression of a particular gene. Preferred components likely to be included with vectors used in the current invention are as follows.

A. Regulatory Elements

As used herein, "increased expression" or "overexpression" can refer to any of the well-known methods for increasing the levels of transcription of an RNA sequence, for example an antisense or inhibitory RNA (RNAi) sequence, or protein produced as a result of gene transcription to mRNA and subsequent translation of the mRNA. Increased expression and overexpression also refer to the substantial and measurable increase in the amount of mRNA in the cell. The transcribed RNA can be in the sense orientation, in the antisense orientation, or in both orientations. Such expression may be effective against a endogenous, native plant gene associated with a trait, or an exogenous gene that may be introduced into the plant.

The use of recombinant DNA molecules for increasing expression of an endogenous gene or overexpressing an exogenous gene in plants is well-known in the art. Exemplary promoters for expression of a nucleic acid sequence include plant promoters such as the CaMV 35S promoter (Odell, et al., Nature 313:810-812, 1985), or others such as CaMV 19S (Lawton, et al., Plant Mol. Biol. 9:315-324, 1987), nos (Ebert et al., Proc. Natl. Acad. Sci. USA 84:5745-5749, 1987), Adh (Walker et al., Proc. Natl. Acad. Sci. USA 84:6624-6628, 1987), sucrose synthase (Yang and Russell, Proc. Natl. Acad. Sci. USA 87:4144-4148, 1990), α-tubulin, actin (Wang et al., Mol. Cell. Biol. 12:3399-3406, 1992), cab (Sullivan et al., Mol. Gen. Genet., 215:431-440, 1989), PEPCase (Hudspeth and Grula, Plant Mol. Biol. 12:579-589, 1989) or those promoters associated with the R gene complex (Chandler et al., The Plant Cell 1:1175-1183, 1989). Tissue-specific promoters such as leaf-specific promoters, or tissue-selective promoters (e.g., promoters that direct greater expression in leaf primordia than in other tissues), and tissue-specific enhancers (Fromm, et al., Nature 319:791-793, 1986) are also contemplated to be useful, as are inducible promoters such as ABA- and turgor-inducible promoters. Any suitable promoters known in the art may be used to express a nucleic acid sequence in accordance with the invention in a plant. In one embodiment, such a nucleic acid sequence may encode a DNA sequence that results in increased expression or overexpression of a miR156 sequence, or down-regulation of a SPL4 gene, or both, in a plant. In a particular embodiment of the invention, the CaMV35S promoter or a native promoter may be used to express a nucleic acid sequence that results in increased expression or overexpression of a miR156 sequence, down-regulation of a SPL4 gene, or both, in a plant.

The DNA sequence between the transcription initiation site and the start of the coding sequence, i.e., the untranslated leader sequence, can also influence gene expression. One may thus wish to employ a particular leader sequence with a transformation construct of the invention. In one embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of nucleic acid sequences targeting a SPL4 gene in a plant.

It is envisioned that nucleic acid sequences targeting a SPL4 gene may be introduced under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters, which have higher activity in roots.

B. Transcription Terminating Sequences

Transformation constructs prepared in accordance with the invention may include a 3' end DNA sequence that acts as a signal to terminate transcription and allow for the polyadenylation of the mRNA produced by coding sequences operably linked to a promoter. In one embodiment of the invention, the native terminator of a SPL4 sequence can be used. Alternatively, a heterologous 3' end may enhance the expression of sense or antisense miR156 sequences, SPL44 sequences, or both. Examples of such sequences that may be used in this context include those from the nopaline synthase gene of *Agrobacterium tumefaciens* (nos 3' end) (Bevan, et al., Nucleic Acids Res. 25:369-385, 1983), the terminator sequence for the T7 transcript from the octopine synthase gene of *Agrobacterium tumefaciens*, and the 3' end of the protease inhibitor I or II gene from potato or tomato. Regulatory elements such as an Adh intron (Callis, et al., Genes Dev. 1:1183-1200, 1987), sucrose synthase intron (Vasil, et al., Plant Physiol. 91:1575-1579, 1989) or TMV omega element (Gallie, et al., The Plant Cell 1:301-311, 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., β-glucuronidase (GUS), green fluorescent protein (GFP), or yellow fluorescent protein (YFP)). Of course, many examples of suitable marker proteins are known to the art and can be employed in the practice of the invention.

Many selectable marker coding regions are known and could be used with the present invention including, but not limited to, neo (Potrykus, et al., Mol. Gen. Genet., 199:183-188, 1985), which provides kanamycin resistance and can be selected for using kanamycin, G418, paromomycin, etc.; bar, which confers bialaphos or phosphinothricin resistance; a mutant EPSP synthase protein (Hinchee, et al., Bio/Technol. 6:915-922, 1988) conferring glyphosate resistance; a nitrilase such as bxn from *Klebsiella ozaenae* which confers resistance to bromoxynil (Stalker, et al., Science 242:419-422, 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., J. Biol. Chem. 263:12500-12508, 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, causing rapid accumulation of ammonia and cell death.

One beneficial use of the sequences provided by the invention may be in the alteration of plant phenotypes by genetic transformation with nucleic acid molecules encoding miR156 sequences, SPL4 inhibitory sequences, or both. Such nucleic acid molecules may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize co-transformation.

II. Antisense and RNAi Constructs

Antisense and RNAi treatments represent one way of altering agronomic characteristics in accordance with the invention such as by down-regulation of SPL4. In particular, constructs comprising a SPL4 coding sequence, including fragments thereof, in antisense orientation, or combinations of sense and antisense orientation, may be used to decrease or effectively eliminate the expression of a SPL4 gene in a plant and to alter agronomic characteristics. Accordingly, this may be used to partially or completely "knock-out" the function of a SPL4 sequence, or homologous sequences thereof.

Techniques for RNAi suppression are well-known in the art and are described in, for example, Lehner, et al., (Brief Funct. Genomic Proteomic 3:68-83, 2004) and Downward (BMJ, 328:1245-1248, 2004). The technique is based on the fact that double stranded RNA is capable of directing the degradation of messenger RNA with sequence complementary to one or the other strand (Fire et al., Nature, 391:806-811, 1998). Therefore, by expression of a particular coding sequence in sense and antisense orientation, either as a fragment or longer portion of the corresponding coding sequence, the expression of that corresponding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNAs, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 17, 18, 19, 20, 21, 25, 30, 50, 75 or 100 or more contiguous nucleic acids of the nucleic acid sequence of a SPL4 gene, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have few base mismatches. For example, sequences of eighteen bases in length may be termed complementary when they have complementary nucleotides at sixteen or seventeen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well-known in the art (e.g., Reynolds, et al., Nat. Biotechnol. 22:326-330, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

III. Genetic Transformation

Additionally provided herein are transgenic plants transformed with a recombinant vector as described herein encoding or producing a miR156 sequence, a SPL4 inhibitory sequence, or both, or a sequence modulating expression thereof. In one embodiment, the disclosure provides a transgenic plant or plant cell comprising a polynucleotide molecule or a recombinant DNA construct as described herein, wherein the polynucleotide molecule or recombinant DNA construct encodes or produces a miR156 sequence, a SPL4 inhibitory sequence, or both, or a variant or homologue thereof. In a certain embodiment, the polynucleotide molecule or a recombinant DNA construct may result in the increased expression or overexpression of miR156, down-regulation of SPL4, or both, in the plant. The disclosure therefore also provides progeny of these plants, vegetative, propagative, and reproductive parts of the plants comprising a transgene encoding a miR156 sequence, a SPL4 inhibitory sequence, or both. In some embodiments, a plant in accordance with the present disclosure comprises increased biomass yield and regrowth after cutting relative to a plant not comprising such a polynucleotide molecule or DNA construct.

Suitable methods for transformation of plant or other cells for use with the current invention are believed to include virtually any method by which DNA can be introduced into a cell, such as by direct delivery of DNA, by *Agrobacterium*-mediated transformation (U.S. Pat. Nos. 5,591,616 and 5,563,055; both specifically incorporated herein by reference) by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well-known in the art. See, for example, the methods described by Fraley, et al. (Bio/Technology, 3:629-635, 1985), Rogers, et al. (Methods Enzymol., 153:253-277, 1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*- mediated transformation has been routinely used with dicotyledonous plants for a number of years, including alfalfa, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (U.S. Pat. No. 5,591,616, specifically incorporated herein by reference in its entirety), wheat (McCormac, et al., Mol. Biotechnol. 9:155-159, 1998), barley (McCormac, et al., 1998) and maize (Ishida, et al., Nat. Biotechnol. 14:745-750, 1996).

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, Mol. Biotechnol. 2:135-145, 1994; Lazzeri, Methods Mol. Biol. 49:95-106, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazzeri, 1995), sorghum (Battraw and Hall, Theor. Appl. Genet. 82:161-168, 1991), maize, wheat (He et al., Plant Cell Rep. 14:192-196, 1994) and tomato.

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala, et al., Plant Mol. Biol. 24:317-325, 1994; Hensgens, et al., Plant Mol. Biol. 22:1101-1127, 1993), wheat (U.S. Pat. No. 5,563,055, specifically incorporated herein by reference in its entirety), rice (Hensgens, et al., 1993), oat (Torbet, et al., Plant Cell Reports 14:635-640, 1995; Torbet, et al., Crop Science 38:226-231, 1998), rye (Hensgens, et al., 1993), sugarcane (Bower et al., Plant Journal 2:409-416, 1992), and sorghum (Casa, et al., Proc. Natl. Acad. Sci. USA 90:11212-11216, 1993); as well as a number of dicots including tobacco (Tomes, et al., Plant. Mol. Biol. 14:261-268, 1990; Buising and Benbow, Mol. Gen. Genet. 243:71-81. 1994), soybean (U.S. Pat. No. 5,322,783, specifically incorporated herein by reference in its entirety), sunflower (Knittel, et al., Plant Cell Reports 14:81-86, 1994), peanut (Singsit, et al., Transgenic Res. 6:169-176, 1997), cotton (McCabe and Martinell, Bio-Technology 11:596-598, 1993), tomato (VanEck, et al., Plant Cell Reports 14:299-304, 1995), and legumes in general (U.S. Pat. No. 5,563,055, specifically incorporated herein by reference in its entirety).

The transgenic plants of the present invention comprising increased expression or overexpression of miR156, SPL4 inhibitory sequences, or both can be of any species. In some embodiments, the transgenic plant is a dicotyledonous plant, for example an agronomically important plant such as soybean, *Medicago truncatula*, a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or an *Arabidopsis* species. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell.

Also contemplated herein is a plant genetically engineered to exhibit increased expression, or overexpression, of a miR156 sequence, or a SPL4 inhibitory sequence, or both, wherein the protein product (i.e., polypeptide) alters plant morphology. In certain embodiments, the altered plant morphology may be increased biomass yield and regrowth after cutting. Such plants are described in the Examples, and may be useful, e.g., as commercial plants, due to their improved agronomic characteristics.

The plants of these embodiments having increased expression or overexpression of a miR156 sequence, SPL4 inhibitory sequences, or both, can be of any species. The species may be any monocotyledonous or dicotyledonous plant, such as those described herein. One of skill in the art will recognize that the present invention may be applied to plants of other species by employing methods described herein and others known in the art.

Application of these systems to different plant strains depends upon the ability to regenerate that particular plant strain from protoplasts. Illustrative methods for the regeneration of cereals from protoplasts have been described (U.S. Pat. No. 5,508,184; specifically incorporated herein by reference in its entirety). Examples of the use of direct uptake transformation of cereal protoplasts include transformation of rice (Ghosh-Biswas, et al., Plant Cell Rep. 13:528-

532, 1994), sorghum (Battraw and Hall, 1991), barley (Lazzeri, 1995), oat (Zheng and Edwards, J. Gen. Virol. 71:1865-1868, 1990) and maize (Omirulleh, et al., Plant Mol. Biol. 21:415-428, 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

IV. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent Application Publication No. WO 97/4103.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 week on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and polymerase chain reaction (PCR); "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of an exogenous gene through the use of techniques well-known to those skilled in the art. Note that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Both PCR and Southern hybridization techniques can be used to demonstrate transmission of a transgene to progeny. In most instances the characteristic Southern hybridization pattern for a given transformant will segregate in progeny as one or more Mendelian genes indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

While Southern blotting and PCR may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

The expression of a gene product is often determined by evaluating the phenotypic results of its expression. These assays also may take many forms including but not limited to analyzing changes in the chemical composition, morphology, or physiological properties of the plant. Chemical composition may be altered, for instance, by expression of genes encoding enzymes or storage proteins which change amino acid composition and may be detected by amino acid analysis, or by enzymes that change starch quantity which may be analyzed by near infrared reflectance spectrometry. Morphological changes may include, for instance, larger seeds, larger seed pods, larger leaves, greater stature, thicker stalks, and altered leaf-stem ratio, among others. Most often changes in response of plants or plant parts to imposed treatments are evaluated under carefully controlled conditions termed bioassays.

V. Breeding Plants of the Invention

In addition to direct transformation of a particular plant genotype with a construct prepared according to the current invention, transgenic plants may be made by crossing a plant having a recombinant DNA molecule of the invention to a second plant lacking the construct. For example, a recombinant nucleic acid sequence producing a miR156 sequence, a SPL4 inhibitory sequence, or both, can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

Down-regulation: The reduction in the expression of a DNA or RNA transcript and/or the function or activity of a protein relative to a control or naturally-occurring counterpart.

Expression: The combination of intracellular processes, including transcription and translation, undergone by a coding DNA molecule such as a structural gene to produce a polypeptide. A plant in accordance with the invention may exhibit altered expression of a gene set forth herein. Such altered expression may include increased expression, decreased expression, or complete absence of expression.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. The sequence may also be altered, i.e., mutated, with respect to the native regulatory sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Recombinant DNA molecule: A synthetic nucleic acid sequence including at least one genetic element which can be introduced, or has introduced, into a plant genome by genetic transformation.

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

Although this specification discloses advantages in the context of certain illustrative, non-limiting embodiments, various changes, substitutions, permutations, and alterations may be made without departing from the scope of the appended claims. Further, any feature described in connection with any one embodiment may also be applicable to any other embodiment.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Plant Materials and Growth Conditions.

All genotypes (AP13, ST2 and NFCX1) applied in the present Examples are derived from lowland-type switchgrass cultivar Alamo (2n=4x=36). Plants were grown in the greenhouse at 26° C. with 16 h light (390 µE·m$^{-2}$·s$^{-1}$). The identification of switchgrass development stages and sample harvesting followed the criteria described by Hardin et al., 2013.

Example 2

Gene Constructs and Transformation.

miR156 overexpression transgenic lines were created by applying the previously described OsmiR156b construct (Fu, et al., 2012) to transform genotype NFCX1 following the established protocol (Fu, et al., Proc. Natl. Acad. Sci. USA 108:3803-3808, 2011).

Based on the EST sequences, the full length mRNA sequences of PvSPL4a and 4b were isolated by 5'- and 3'-RACE following protocols from the manufacturer (Invitrogen). To knockdown PvSPL4, an RNAi binary vector was constructed using the pANIC12A gateway vector (Mann, et al., Plant Biotechnol. J. 10:226-236, 2012). A 443-bp SPL4 cDNA fragment selected from the conserved domain was amplified by PCR and cloned into the pANIC12A vector. The verified construct was used to transform NFCX1.

Example 3

Gene Expression Quantification.

Quantitative RT-PCR was performed to analyze transcript abundance of various genes. Total RNA was extracted from various tissues by Tri-Reagent (Invitrogen) and subjected to reverse transcription with Superscript Kit (Invitrogen). SYBR Green (Applied Biosystems, Foster City, Calif.) was used as the reporter dye. Ubq1 transcripts (GenBank accession number: FL899020) were used as an internal control.

The mature miR156 level was quantified by using stem-loop RT-PCR procedure (Cui, et al., Plant J. 80:1108-1117, 2014).

Example 4

Microarray Analysis of miR156 Transgenic Lines.

Total RNA samples from duplicate biological replicates of the selected miR156 transgenic events and the wild type NFCX1 were extracted from node 2 and node 4 meristems at E5 stage using Spectrum™ Plant Total RNA Kit (Sigma-Aldrich). 500 ng RNA was amplified and labeled using the GeneChip 3' IVT Express Kit (Affymetrix, Santa Clara, Calif.) and hybridized to Affymetrix switchgrass cDNA chips. Data normalization was conducted by using the robust multi-array average (RMA). Data analysis of differentially expressed probe sets on the chip was performed by associative analysis as described (Dozmorov and Centola, Bioinformatics 19:204-211, 2003). This analysis revealed that 4,963 genes exhibited significant difference among the 16 samples tested. 605 out of the 4,341 genes' abundance changed more than twofold in the events with well-developed buds than in the events lacking buds and the wild-type control. Since axillary bud formation was established in node 2 yet still underway in node 4, the bud regulation genes were therefore differently expressed in node 4 only. Applying this criterion, hierarchical analysis further indicated that 48 out of the 605 genes exhibited a highly positive correlation between phenotype and gene expression.

Example 5

Characterization of Plant Growth and Development.

Tiller number, fresh biomass were measured when plants reached R1 stage. Then, the harvested biomass was dried in an oven at 45° C. for 96 h to measure the dried biomass.

Example 6

Microscopy Analysis and Photography.

Axillary buds and related node samples were harvested and immediately fixed in fixative solution (3% glutaraldehyde in 25 mM phosphate buffer, pH 7.0) overnight, dehydrated in graded ethanol series. The fixed and dried samples were observed by using Hitachi™-3000 scanning electron microscope. Light microscopy was performed using a Nikon SMZ 1500 stereomicroscope (Nikon).

Example 7

Subcellular Localization of YFP-PvSPL4.

The conserved coding sequence of PvSPL4 from NFCX1 was cloned into a pEarleyGate104 vector to generate an YFP-SPL4 fusion protein with the YFP tag at N terminus. NFCX1 callus was transformed with this construct by following the protocol previously described by the inventors (Fu, et al., 2011). Root samples were observed using a Leica TCS SP2AOBS confocal laser scanning microscope using the 488-nm line of an argon laser for the YFP signal, and emission was detected at 510 nm.

Example 8

RNA-Seq Analysis of the Regulation Mechanism of Bud Development.

Total RNA samples from duplicate biological replicates of the selected PvSPL4-RNAi transgenic events and the wild type NFCX1 were extracted from node 4 meristems at E5 stage using Spectrum™ Plant Total RNA Kit (Sigma-Aldrich). All reads were quality trimmed before mapping, removing bases from the end of the read until two consecutive bases with quality scores of 30 or higher were found. Reads less than 30 bases long after trimming were discarded, along with their mate pair. The trimmed reads were then mapped to the Panicum virgatum v1.1 genome sequence using Tophat 2.0.12 with 24 threads, an average mate inner distance of 100 bp, mate distance standard deviation of 50, and a maximum intron length of 25000 bp. Transcripts were assembled and quantified using Cufflinks 2.2.1 with the default assembly parameters. The transcripts identified in all samples in the study were then compiled into a unified set of transcripts and compared with the Panicum virgatum v1.1 annotated transcripts using Cuffcompare 2.2.1. Differential expression testing was performed using the default settings of Cuffdiff 2.2.1.

Example 9

Phytohormone Quantification.

Node aerial axillary meristem tissues of nodes 2 and 3, the surrounding tissues of the meristems (named as surrounding tissue) of nodes 2 and 3, and entire stems were harvested from wild-type NFCX1 and PvSPL4Ri plants at E5 stage. Harvested samples were frozen in liquid $N_2$ and well ground immediately. 50 mg of each sample was applied for hormones quantification with HPLC-MS analysis as described (Pan et al., Nat. Protoc. 5:986-992, 2010).

Example 10

Identification of M. truncatula Mutants.

Six putative mutant lines were found by blasting against the database of Medicago truncatula Tnt1 mutants (medicago-mutant.noble.org/mutant/index.php) using the MtSPL4 cDNA sequence. PCR analysis confirmed that three out of the six lines contain the retrotransposon Tnt1 insertion in exons of MtSPL4. The three mutants were named spl4-1, spl4-2 and spl4-3.

Example 11

Genetic Transformation of M. truncatula.

The MtSPL4 cDNA isolated from M. truncatula ecotype R108 was cloned into the pEarleyGate100 vector. The construct was introduced into Agrobacterium strain EHA105 using the freezing/heat shock method. Leaf explants from R108 were used for stable transformation. Regenerated M. truncatula plants were grown in the greenhouse at 22° C. day/20° C. night temperature, 16-h-day/8-h-night photoperiod.

Example 12

Micropropagation by Node Culture is Based on the Formation of Aerial Buds.

Figure 1:
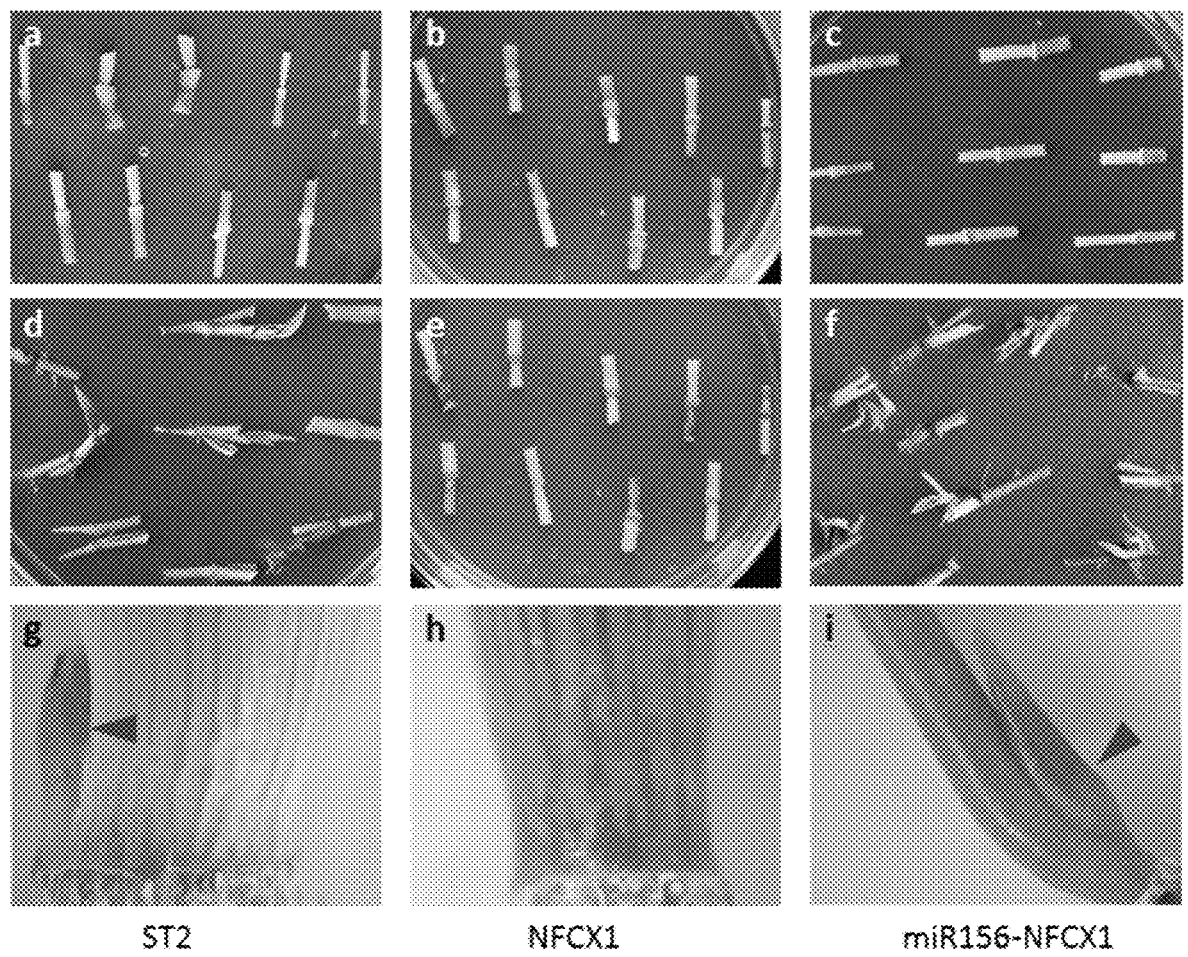
FIG. 1—Panels a-h show responses of different switchgrass genotypes to node culture.
Figure 7:
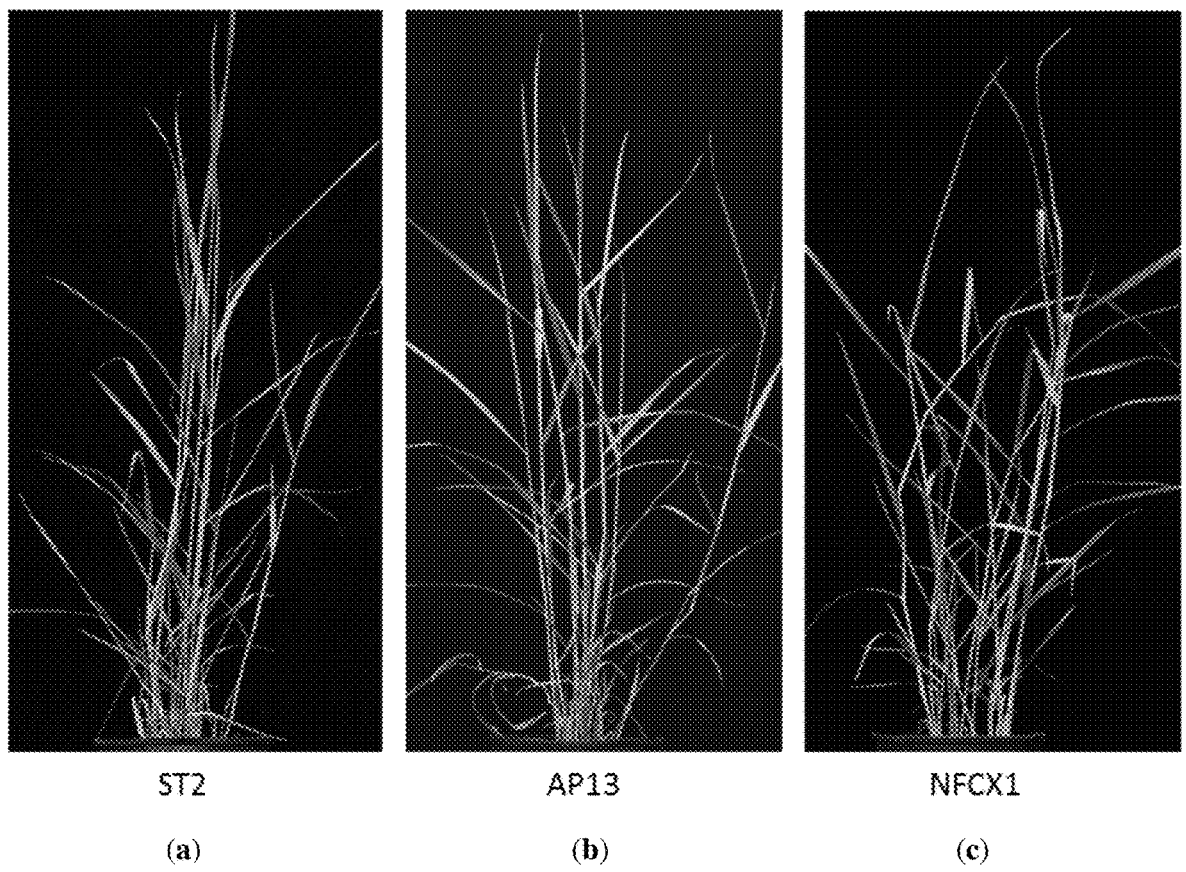
FIG. 7—Panels a-c show morphological performance of switchgrass genotypes ST2 (FIG. 7 panel a), AP13 (FIG. 7 panel b) and NFCX1 (FIG. 7 panel c).
Figure 8:
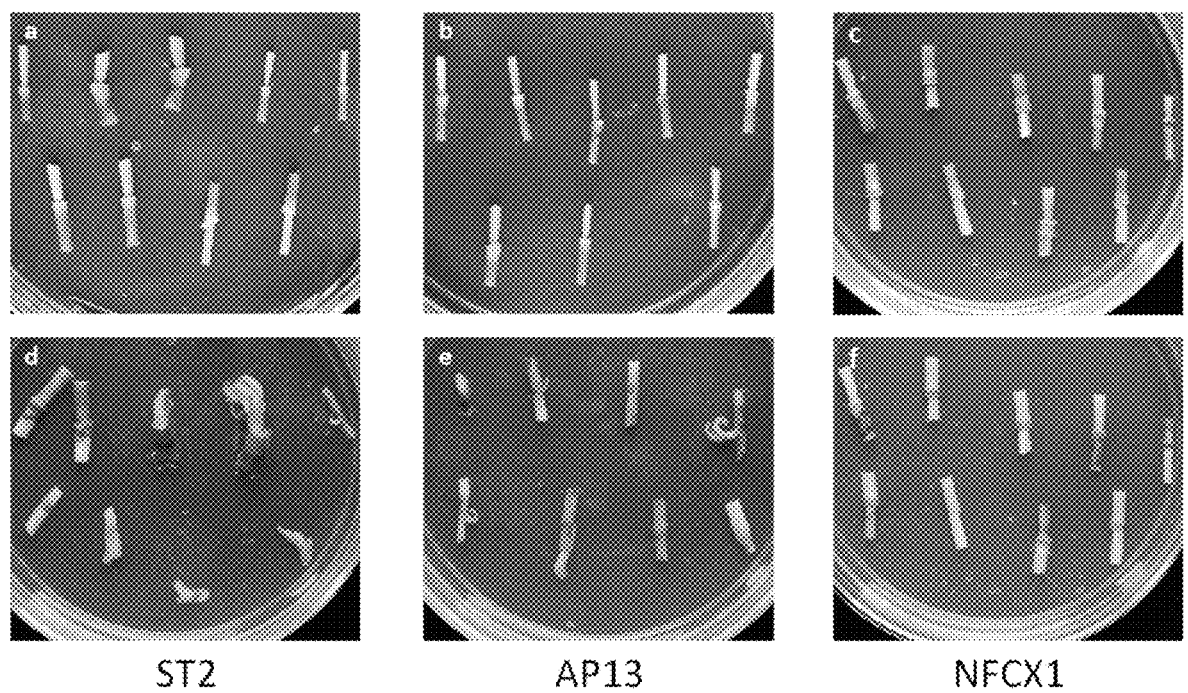
FIG. 8—Panels a-f show node culture results of switchgrass genotypes ST2 (FIG. 8 panels a and d), AP13 (FIG. 8 panels b and e) and NFCX1 (FIG. 8 panels c and f).
Figure 9:
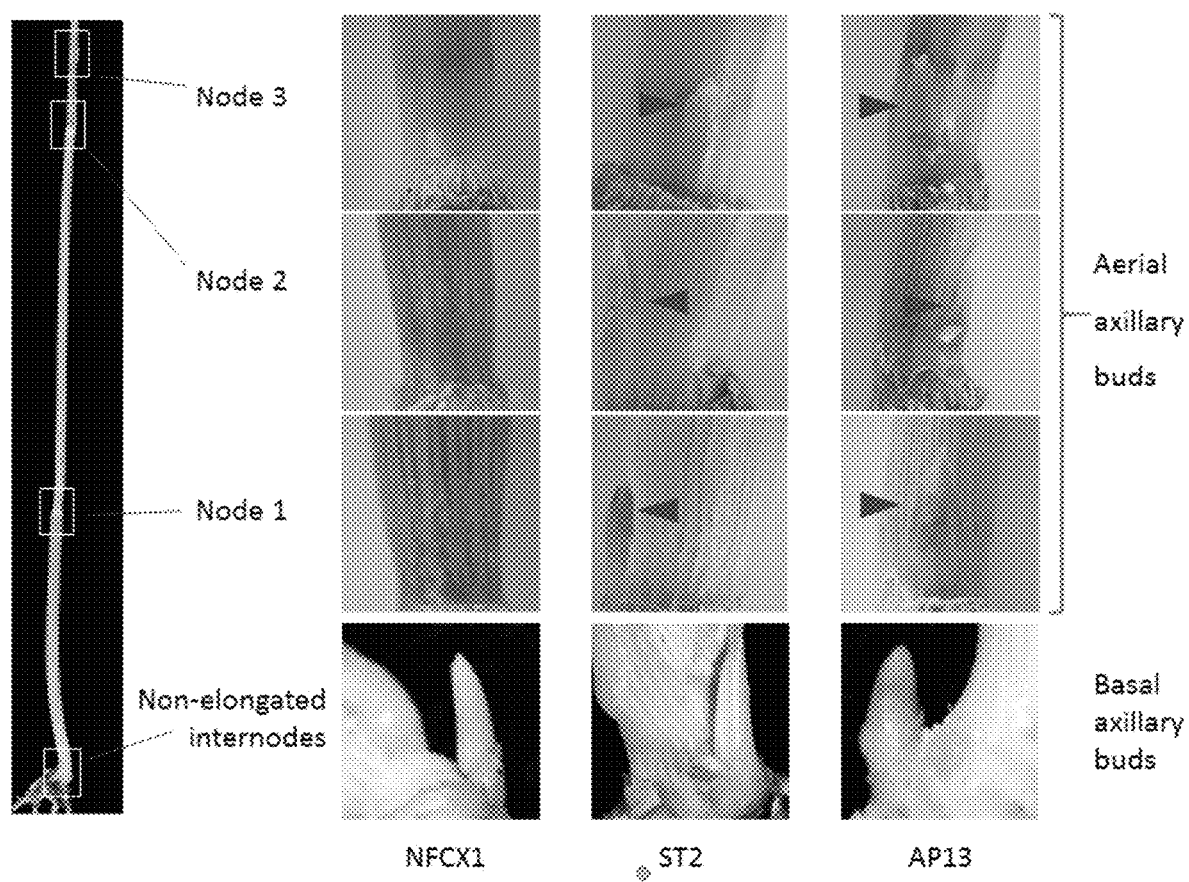
FIG. 9—Show axillary buds development in different switchgrass genotypes. The first panel shows the location of nodes 1-3 and the non-elongated internodes. Genotype NFCX1 has no aerial axillary buds in node 3, node 2, or node 1. In contrast, genotypes ST2 and AP13 have well developed axillary buds (arrows) in node 3, node 2, and node 1, especially in the lower nodes. The basal axillary buds from NFCX1, ST2 and AP13 are also shown.

As an outcrossing species, switchgrass is self-incompatible; individual seeds within a cultivar may represent different genotypes (Wang and Ge, In Vitro Cell. Dev. Biol.-Plant 42:1-18, 2006). This means that it is almost impossible to maintain a unique genotype through seeds in switchgrass. For this reason, node culture, a method of mass vegetative propagation (micropropagation), was developed (Alexandrova, et al., Crop Sci. 36:1709-1711, 1996). While doing experiments on node culture, it was unexpectedly found that some genotypes were not responsive to micropropagation. Three genotypes (ST2, AP13 and NFCX1) were then selected from the commonly used switchgrass cultivar, Alamo, and detailed analyses were carried out. The three genotypes were very similar in morphology (FIG. 7) but exhibited different node culture results. Both ST2 and AP13 were easily propagated while NFCX1 had no response to node culture (FIG. 1A-FIG. 1E, FIG. 8). After examining node morphological structures, it was found that both ST2 and AP13 displayed intact aerial buds enclosed between the culm and the sheath in each node, especially in the lower (older) nodes (FIG. 1G, FIG. 9). However, no aerial buds were found in any nodes of NFCX1 (FIG. 1H, FIG. 9). All the three genotypes shared similar basal buds (FIG. 9). The results indicate that the lack of aerial buds leads to the failure of node culture in the genotype NFCX1.

Example 13

Basal and Aerial Buds have Similar Structure but Also Exhibit Differences.

Figure 10:
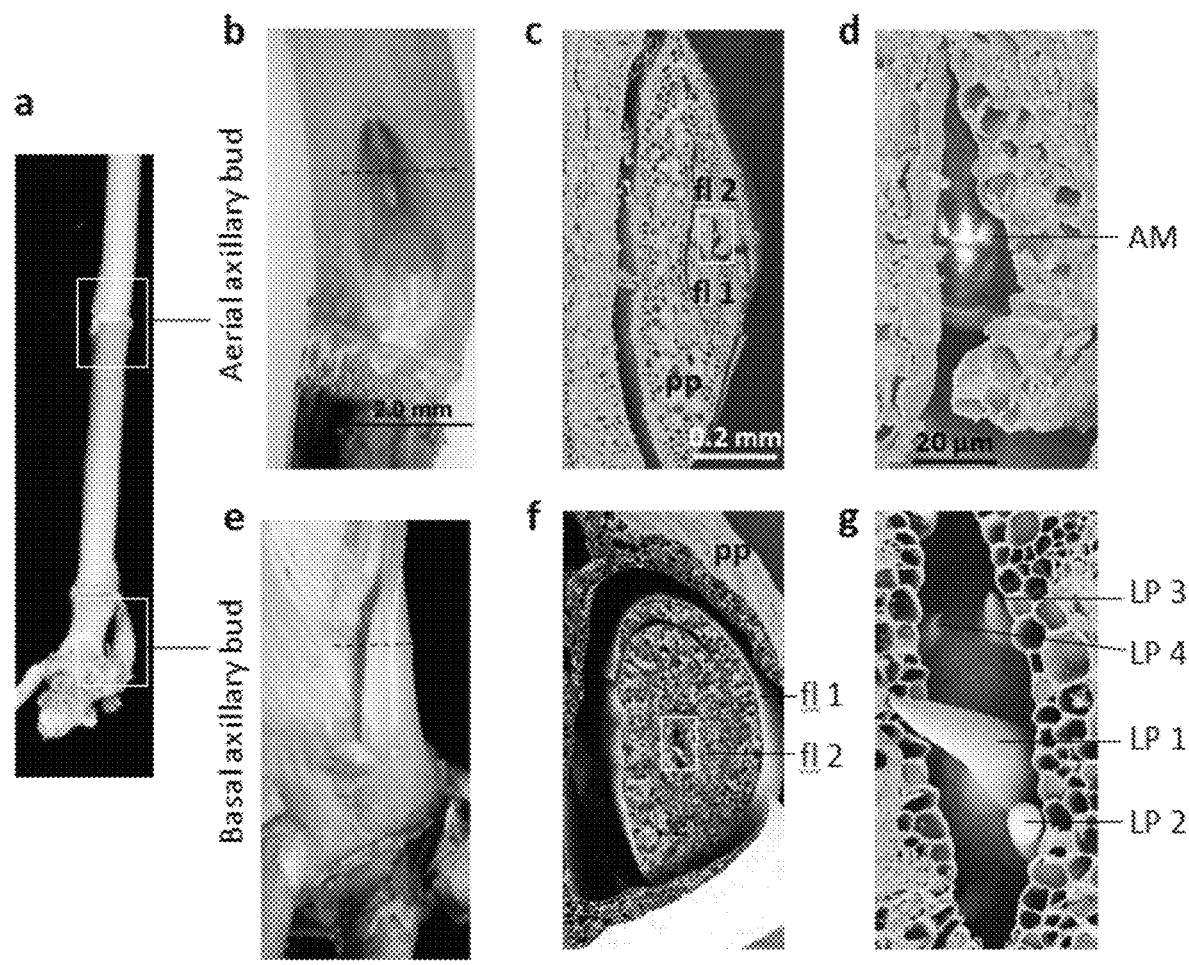
FIG. 10—Panels a-g show exterior appearance and interior structure of aerial and basal axillary buds.

Although basal and aerial buds arose from different positions (FIG. 10A), they have similar appearance and structure in both AP13 and ST2 (FIG. 10B and FIG. 10E). Scanning Electron Microscope (SEM) observation showed that both types of buds have two foliage leaves surrounding the apical meristems and the buds are enclosed by the prophylls (FIG. 10C and FIG. 10F). However, prominent differences were observed at the apical meristems. The basal bud clearly has 3 to 4 distinct leaf primordia spirally located on the apical meristem (FIG. 10G), whereas the aerial buds only exhibit the apical meristem (FIG. 10D). This indicates that aerial bud development is arrested and becomes dormant after initiation. In contrast, basal buds continue developing to the outgrowth stage and subsequently form tillers. The similarities and distinctions between basal and aerial buds imply that they share certain regulatory mechanisms, but their activation is different.

Example 14

Axillary Bud Formation is Regulated by miR156.

Figure 2:
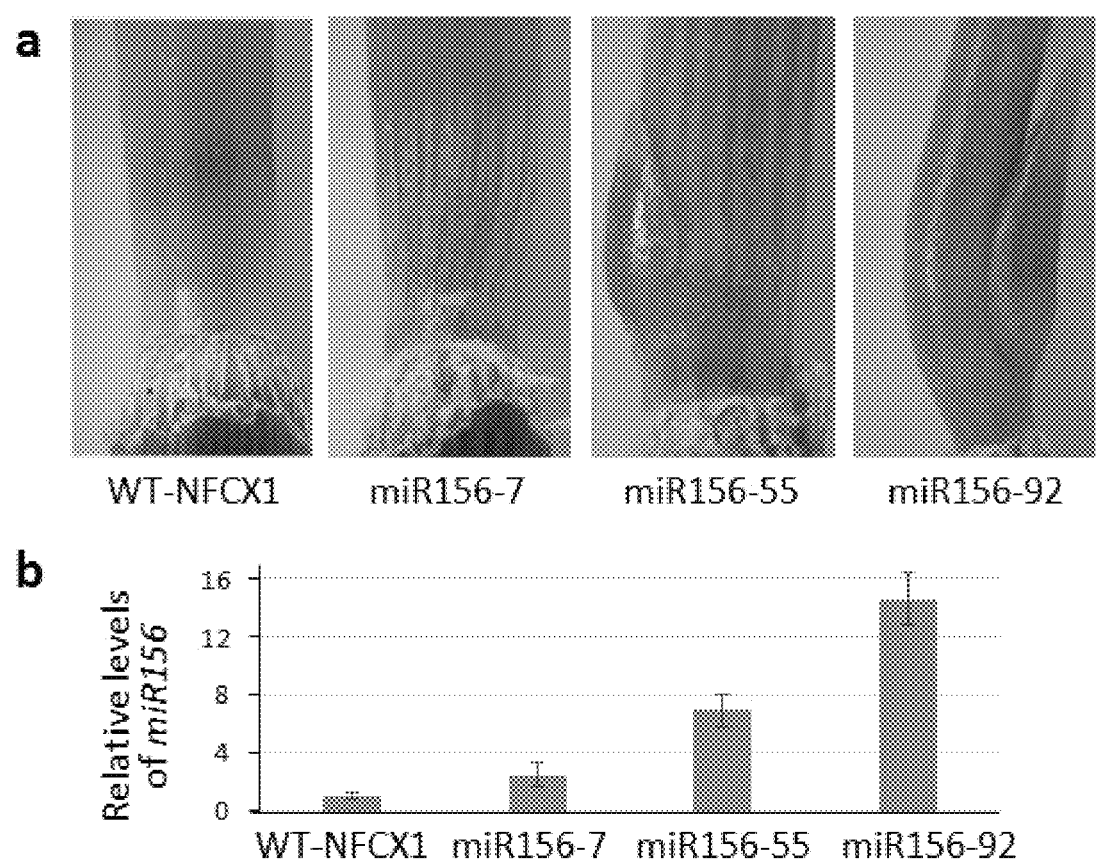
FIG. 2—Panels a and b show aerial axillary bud formation in miR156 overexpression transgenic plants (miR156).

Overexpression of miR156 has been reported to significantly increase tiller numbers in rice (Xie, et al., 2006) and switchgrass (Fu, et al., 2012; Chuck, et al., 2012), although the changes in axillary buds were not observed. Because tillers are derived from basal buds, the results suggest that miR156 plays a role in basal bud development. To elucidate whether or not miR156 is involved in aerial bud formation, miR156 was overexpressed in genotype NFCX1 which has no aerial buds. Aerial buds were successfully induced in NFCX1 (FIG. 2A) along with an increase in basal buds. Furthermore, the induction of aerial buds was highly correlated with the miR156 levels in these transgenic lines (FIG. 2B). In contrast to the wild-type NFCX1 (WT-NFCX1), the transgenics allowed the successful carrying out of node culture and regeneration of shoots (FIG. 1C and FIG. 1F). These results demonstrated that miR156 directly regulates both aerial and basal bud formation. In addition, the results further confirmed that node culture is directly determined by the presence of aerial buds.

Example 15

Microarray and Hierarchical Analyses Identify Specific miR156 Targets Associated with Aerial Bud Formation.

Figure 11:
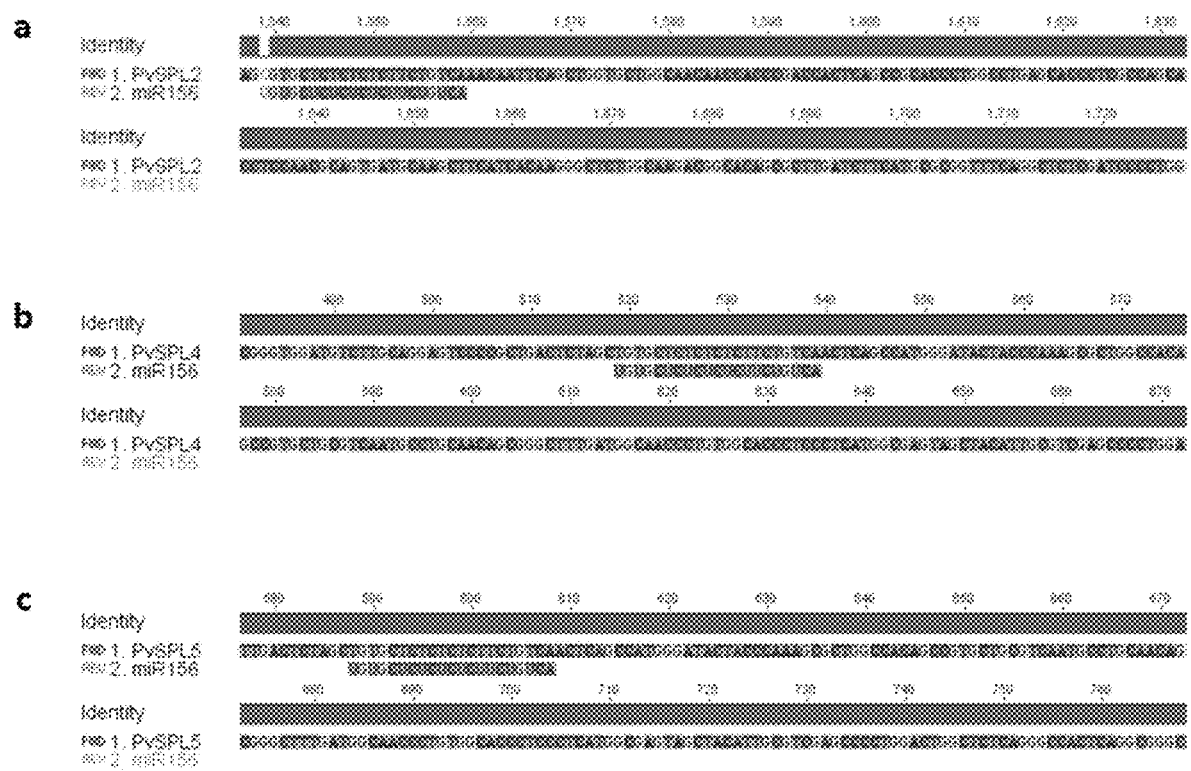
FIG. 11—Panels a-c show sequence analyses of PvSPL2 (SEQ ID NO:12), PvSPL4 (SEQ ID NO:13), PvSPL5 (SEQ ID NO:14) and miR156 (SEQ ID NO:15). Sequence blast indicates that PvSPL2 (FIG. 11 panel a), PvSPL4 (FIG. 11 panel b) and PvSPL5 (FIG. 11 panel c) contain the target sequence of miR156.

Three miR156 transgenic lines that varied in aerial bud formation (from total absence to well-developed buds; FIG. 2A) were selected for microarray analysis. From each line, tillers at E5 stage (with 5 visible internodes, see FIG. 9) were harvested and node axillary meristems excised separately from two different nodes (node 2 with developed bud, node 4 with initiating bud primordia) from each tiller. Microarray analysis revealed that 4,963 genes exhibited significant differences between the tested samples. By hierarchical analysis 48 genes were further identified exhibiting strong positive correlations between the phenotype and gene expression levels. Further gene annotation revealed that 3 of the 48 genes, PvSPL2, PvSPL4 and PvSPL5, contain the target sequence of miR156 (FIG. 11).

Example 16

The Expression of PvSPL4 and 5 is Highly Correlated with Aerial Bud and Tiller Formation.

Figure 3:
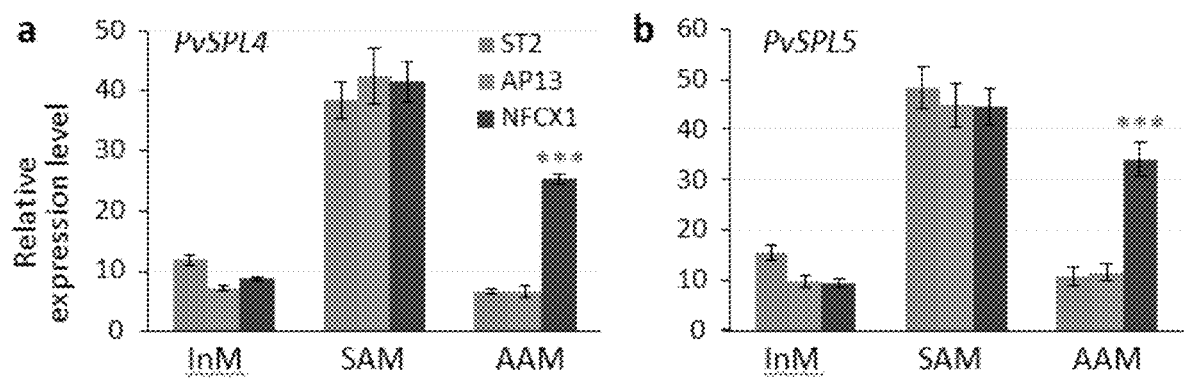
FIG. 3—Panels a and b show transcript levels of PvSPL4 (FIG. 3 panel a) and PvSPL5 (FIG. 3 panel b) determined by qRT-PCR. Higher transcript levels were detected in NFCX1 node meristems. InM, inflorescence meristems; SAM, shoot apical meristems; AAM, node aerial axillary meristems. Values represent mean±S.D. of three replicates. ***p<0.001.
Figure 4:
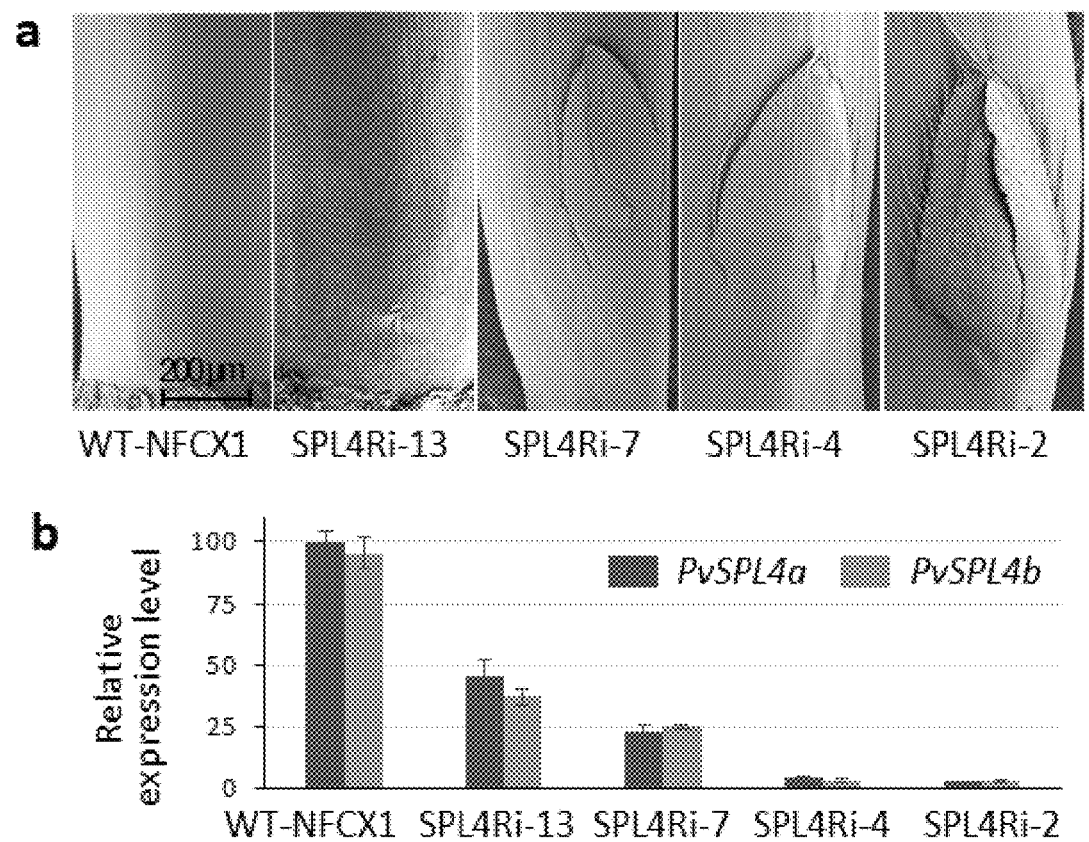
FIG. 4—Panels a and b show aerial axillary bud formation in PvSPL4-RNAi transgenic plants (SPL4Ri).
Figure 12:
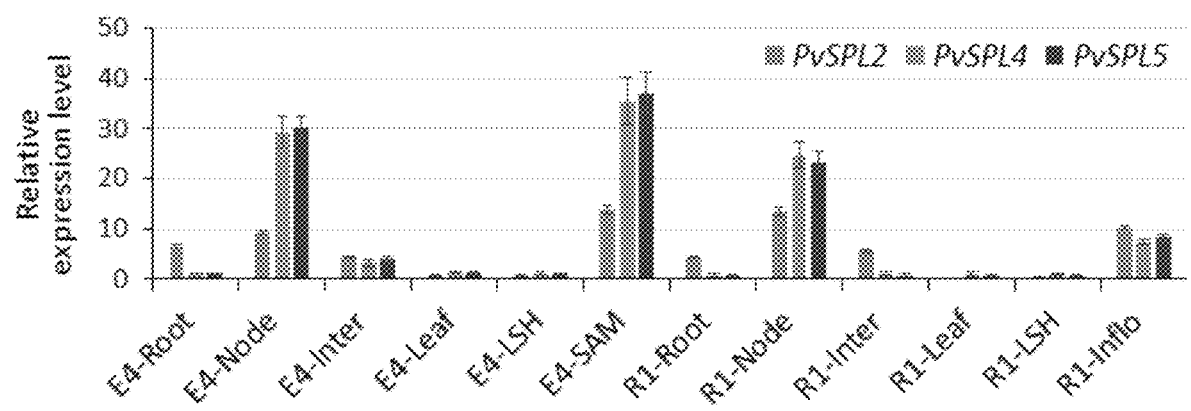
FIG. 12—Shows expression profiles of PvSPL2, PvSPL4 and PvSPL5 in switchgrass genotype NFCX1. Higher transcript levels of PvSPL4 and PvSPL5 were detected in SAM and node at both vegetative stage (E4) and reproductive stage (R1). E4, vegetative growth stage 4; R1, reproductive stage 1; Inter, internode; LSH, leaf sheath; Info, inflorescence meristems; SAM, shoot apex meristems. Values represent mean±S.D. of three replicates.
Figure 13:
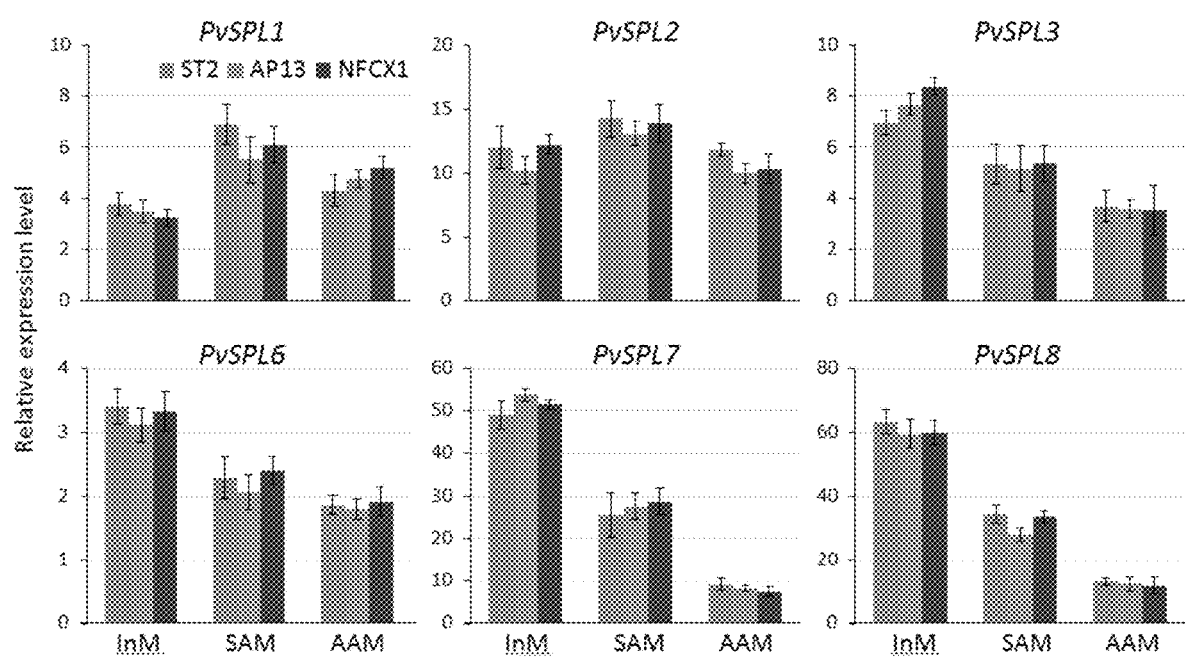
FIG. 13—Show expression of PvSPL1, PvSPL2, PvSPL3, PvSPL6, PvSPL7, and PvSPL8 in various meristem tissues in different switchgrass genotypes. InM, inflorescence meristems harvested at R1 stage; SAM, shoot apical meristems; AAM, node aerial axillary meristems. Values represent mean±S.D. of three replicates.
Figure 14:
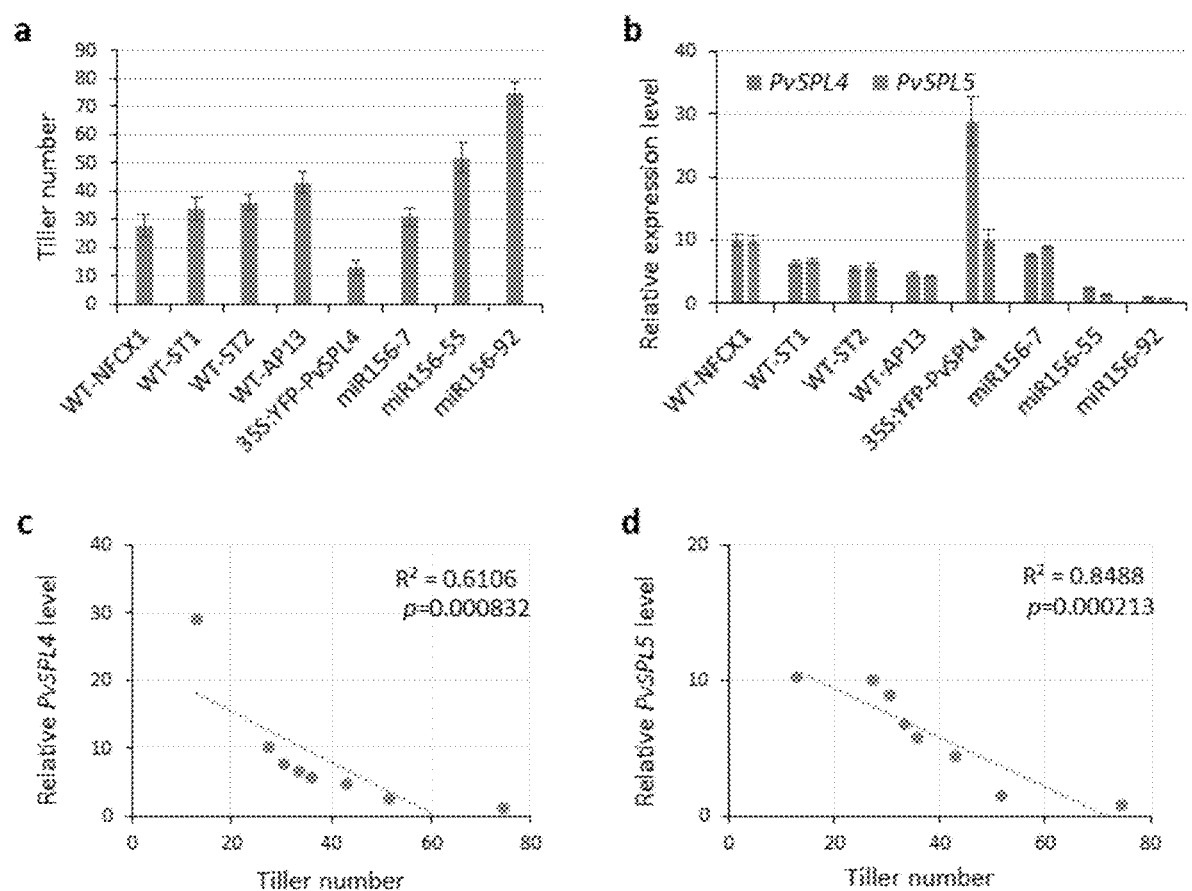
FIG. 14—Panels a-d show relationship between tiller development and the expression levels of PvSPL4 and 5.

To decipher which SPL is the direct regulator of axillary bud formation, expression profiles of these genes was first investigated using switchgrass Gene Atlas (switchgrassgenomics.noble.org/). PvSPL2 is expressed in all tissues at low levels while both PvSPL4 and 5 are highly expressed in node and shoot apex meristems (FIG. 12). The expression of PvSPL4 and 5 was further investigated in all aerial meristems including shoot apex meristems (SAM), node aerial axillary meristems (AAM) and inflorescence meristems (InM) of different genotypes that vary in aerial bud formation (FIG. 9) using real time qRT-PCR. PvSPL4 and 5 did not show any difference in either shoot apex meristems or inflorescence meristems, but exhibited significantly higher expression in the aerial axillary meristems of NFCX1 compared with other genotypes (FIG. 3). This difference is highly associated with the variation of aerial bud formation among these genotypes. Meanwhile, none of the other SPLs showed such differences (FIG. 13). Furthermore, the investigation of PvSPL4 and 5 expression in nodes of four wild types and four transgenic lines with various axillary bud formation showed that plants with lower PvSPL4 and 5 levels have aerial buds and more tillers whereas plants with higher PvSPL4 and 5 levels have no aerial buds and fewer tillers (FIG. 14A and FIG. 14B). Statistical analysis revealed that PvSPL4 and 5 expression is highly correlated with aerial bud formation and tillering (FIG. 14C and FIG. 14D). Taken together, the results suggest that PvSPL4 and 5 directly regulate axillary bud formation.

Figure 16A:
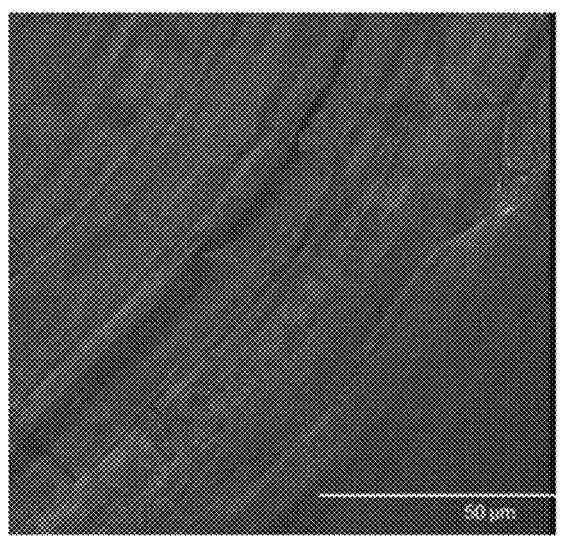
FIG. 16A and FIG. 16B—Show expression of 35S: YFP-SPL4 in switchgrass root by bright field microscopy (FIG. 16A) and YFP inflorescence (FIG. 16B) shows that YFP-SPL4 fusion protein is specifically localized in the nucleus.
Figure 16B:
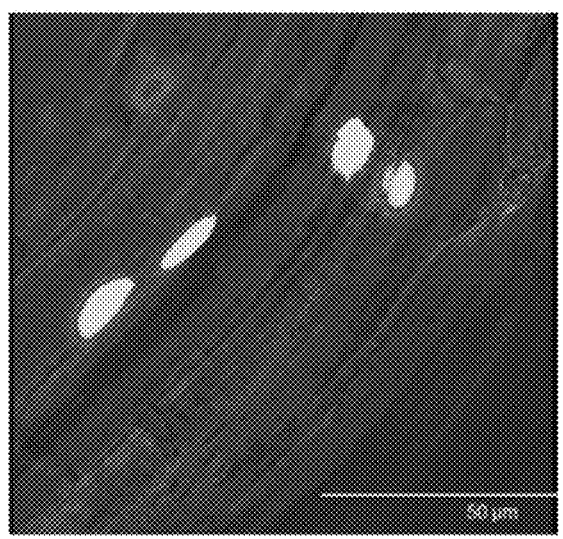

After cloning full length cDNA sequences of PvSPL4 and 5, it was found that they are very similar in the coding region but different in the 5' untranslated region (FIG. 15). BLAST search against the switchgrass genome showed that PvSPL4 and 5 locate at the same locus on chromosome 6. In addition, PvSPL4 and 5 exhibit very similar expression patterns in various tissues and genotypes. All these results suggest that PvSPL4 and 5 are allelic genes. They were therefore renamed as PvSPL4a and PvSPL4b, respectively. YFP-SPL4 fusion protein was localized in the nucleus (FIG. 16). Overexpressing PvSPL4 in WT-NFCX1 resulted in a significant decrease in tillering (FIG. 14A), further indicating that PvSPL4 is involved in inhibition of axillary bud development.

Example 17

Down-Regulation of PvSPL4 Induces Aerial Bud Formation.

Figure 17:
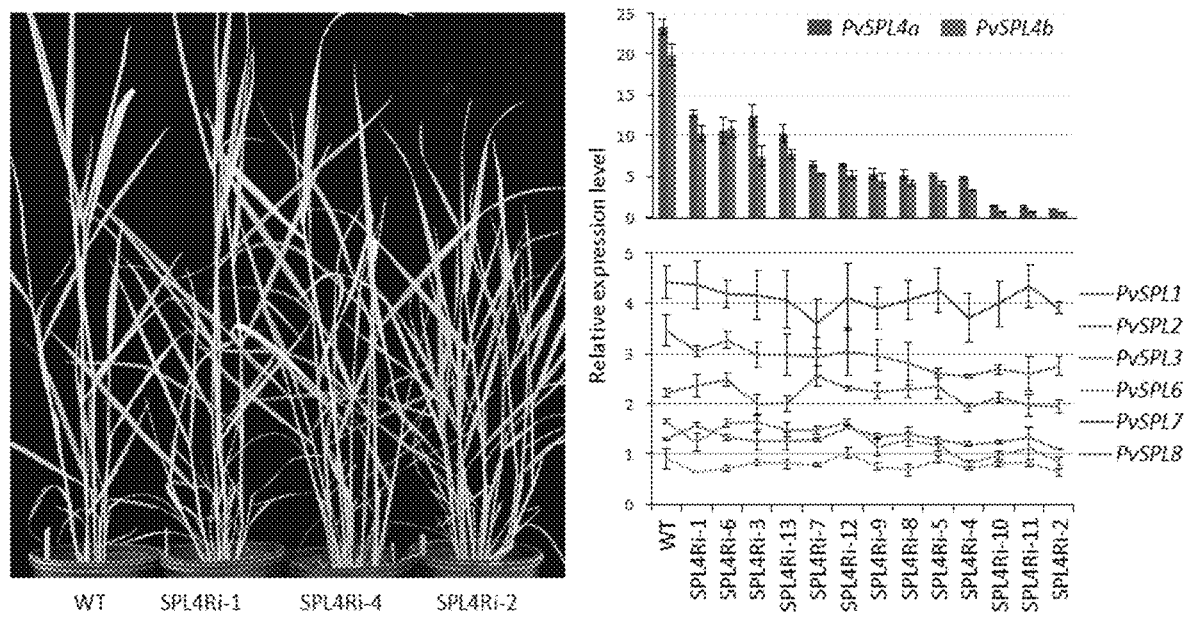
FIG. 17—Shows PvSPL4-RNAi transgenic plants (SPL4Ri) and expression levels of PvSPLs in these plants. The expression levels of both PvSPL4a and PvSPL4b were significantly reduced in the SPL4Ri plants. The other 6 SPLs showed no obvious changes.
Figure 18:
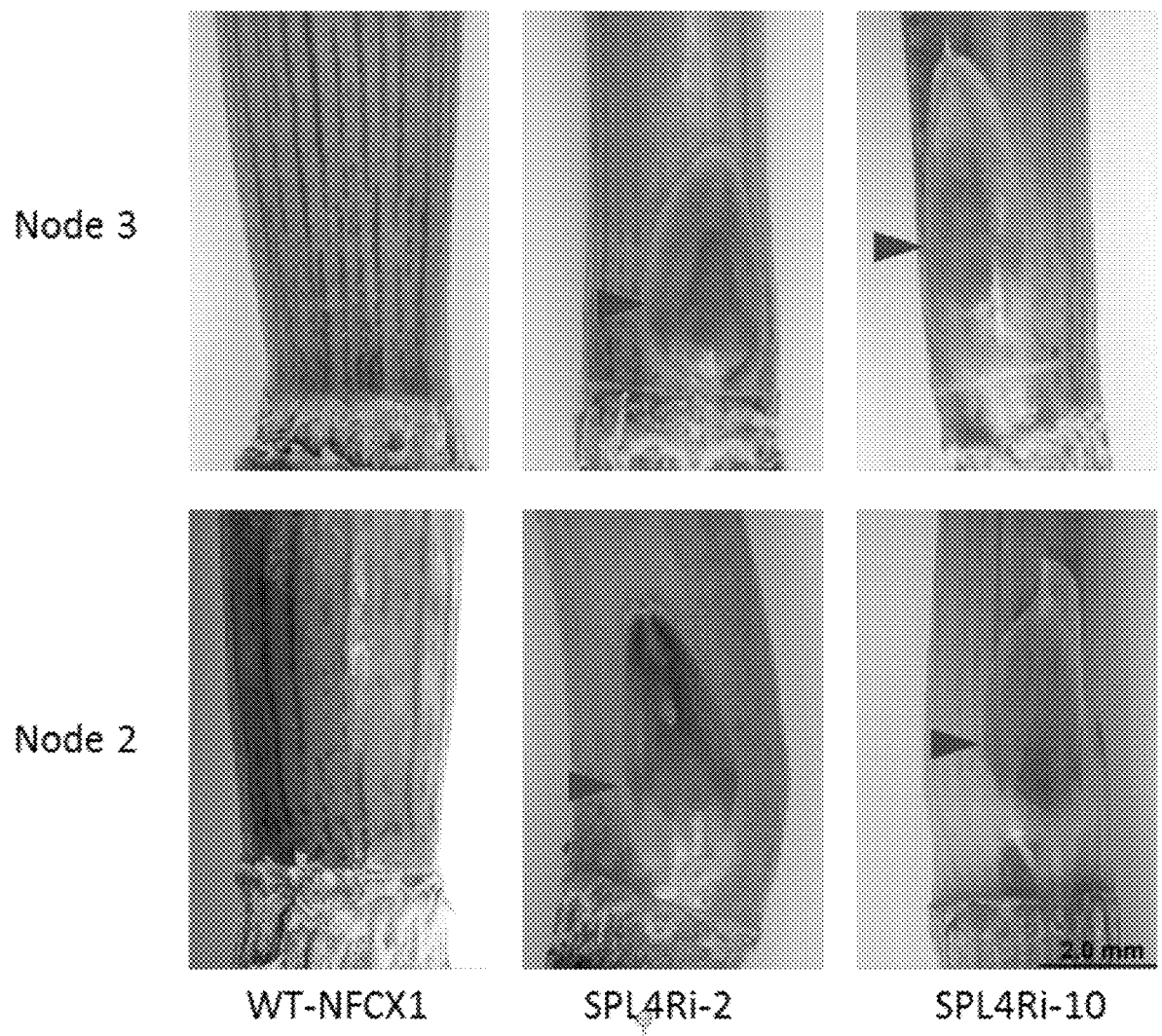
FIG. 18—Shows aerial axillary buds of different nodes of PvSPL4-RNAi transgenic plants SPL4Ri-2 and SPL4Ri-10 compared to WT-NFCX1. Down-regulation of PvSPL4 effectively promoted axillary bud formation in the SPL4Ri-2 and SPL4Ri-10 plants in node 3 and node 2 compared to WT-NFCX1.
Figure 19:
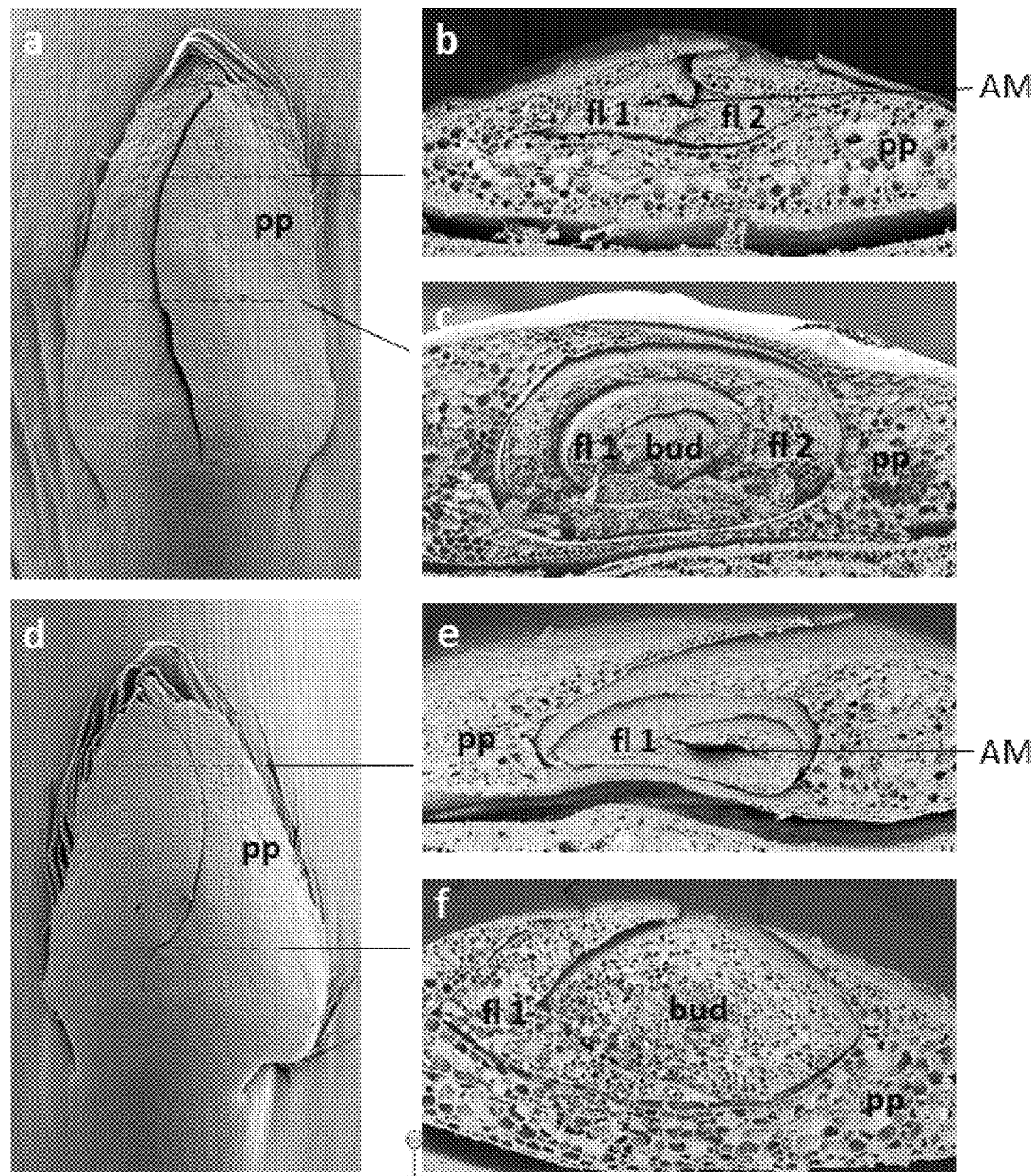
FIG. 19—Panels a-f show comparison of the internal structures of aerial axillary buds of the 3$^{rd}$ node of different plants. Overall structures of the aerial axillary buds of NFCX1 transformed with PvSPL4RNAi construct (FIG. 19 panel a) and wild-type genotype ST2 (FIG. 19 panel d). The dashed lines indicate the positions of cross-sections.

PvSPL4-RNAi construct was introduced into NFCX1 callus, and transgenic plants (SPL4Ri) were produced. qRT-PCR data showed that the expression levels of both PvSPL4a and 4b were dramatically decreased, whereas the other SPLs had no significant expression changes in the SPL4Ri lines (FIG. 17). Examination of the nodes revealed that aerial buds were induced in all transgenic lines with a significant decrease of PvSPL4s expression (FIG. 18).

More detailed observation with SEM showed that while wild-type NFCX1 does not produce any aerial axillary buds (FIG. 4A), transgenic plants with an over 90% reduction of PvSPL4 levels had well developed aerial buds with two foliage leaves in the upper (younger) buds (FIG. 4, FIG. 19A-FIG. 19C). The results indicate that aerial bud development in the heavily down-regulated SPL4Ri lines is more advanced than wild-type ST2 and AP13, because only the older aerial buds in ST2 and AP13 have two foliage leaves (FIG. 19C) while the younger buds have just one foliage leaf (FIG. 19D-FIG. 19F). On the other hand, SPL4Ri plants with a less than 70% decrease of PvSPL4 level failed to restore the formation of aerial buds (FIG. 4), suggesting that in these plants the PvSPL4 expression level is still high enough to suppress bud initiation.

Example 18

Knockdown of PvSPL4 Significantly Increases Tiller Number, Biomass Yield and Regrowth.

Figure 5:
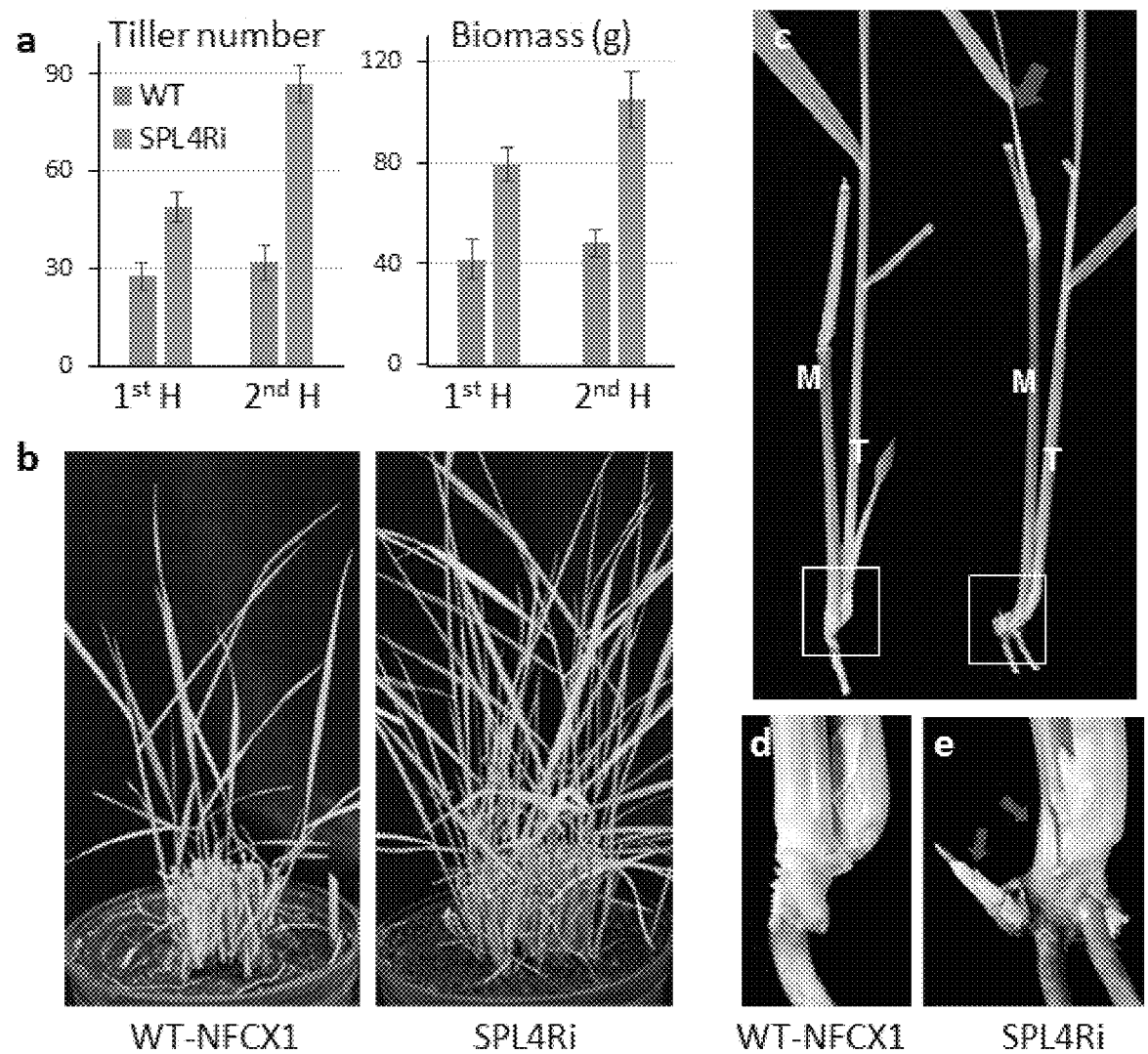
FIG. 5—Panels a-e show phenotype and agronomic performance of PvSPL4-RNAi transgenic plants (SPL4Ri).
Figure 20:
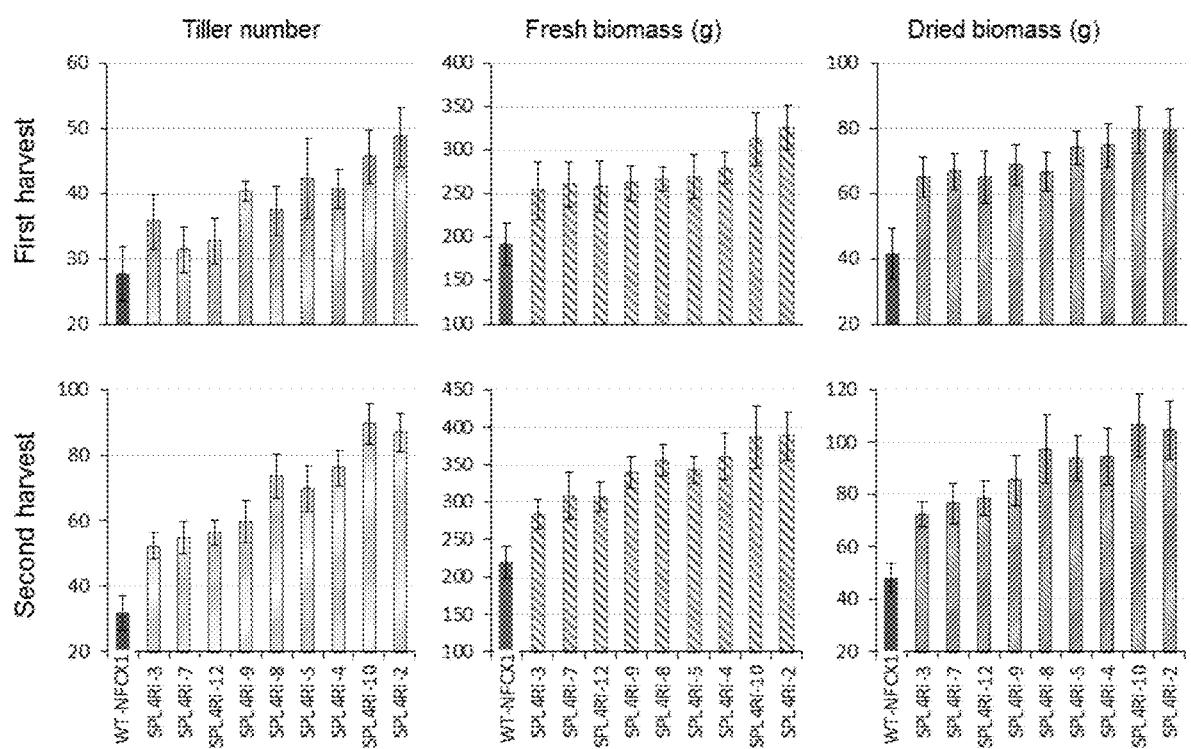
FIG. 20—Shows tiller number and fresh and dried biomass yield of WT-NFCX1 and transgenic lines. Down-regulation of SPL4 increased tiller number and fresh and dried biomass yield in the SPL4-RNAi transgenics compared to the WT-NFCX1, especially in the secondary harvest. Upper panel shows results of the first harvest, lower panel shows results of the secondary harvest. Values represent mean±S.D. of three replicates.

In addition to bud formation, SPL4Ri plants also showed significant improvement in tiller numbers and biomass yield (FIG. 5A). Interestingly, the increases were even more prominent with three- and two-fold gain in tiller number and biomass yield, respectively, in the second harvest after cutting (FIG. 5A, FIG. 20). Essentially, SPL4Ri plants showed dramatically accelerated regrowth after cutting (FIG. 5B). Examinations from independent cut-back experiments revealed that wild-type plants produce one or two basal buds in each tiller after cutting, whereas SPL4Ri lines produce two to four basal buds (FIG. 5C-FIG. 5E). This difference alone enables SPL4Ri lines to form more new tillers than the wild type. Furthermore, it was surprising to find that new branches are also induced in the SPL4Ri plants (FIG. 5C). The combined effects of more tillers and the formation of branches contribute to the significant increase in regrowth and faster regeneration in the SPL4Ri plants compared to wild type. This trait is particularly beneficial for perennial crop species such as switchgrass and alfalfa that are harvested multiple times during the growing season.

Example 19

RNA-Seq Analysis Identifies Possible Down-Stream Regulation Genes of Axillary Bud Formation.

Figure 21:
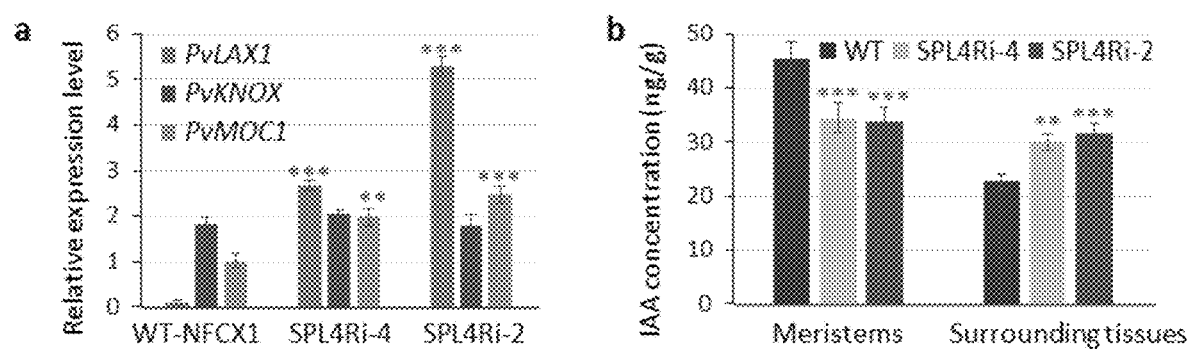
FIG. 21—Panels a and b show expression of bud associated genes (FIG. 21 panel a) and auxin accumulation (FIG. 21 panel b) in WT-NFCX1 and PvSPL4-RNAi transgenic plants (SPL4Ri).
Figure 22:
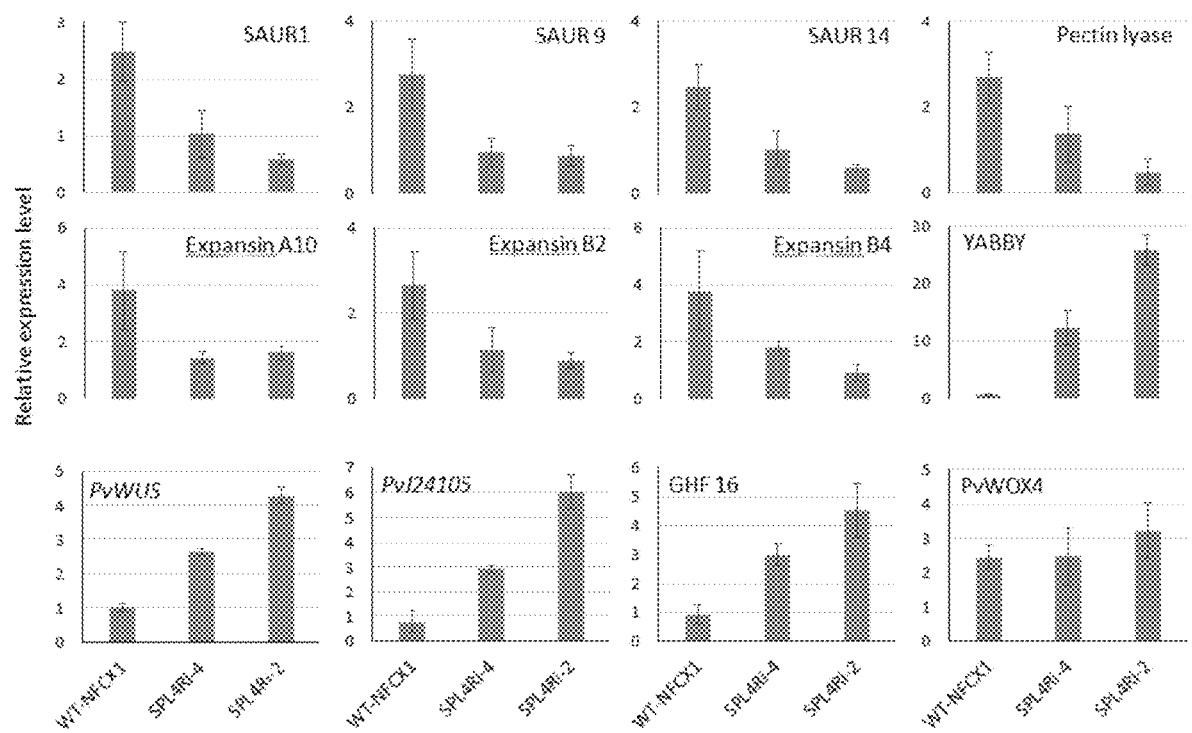
FIG. 22—Shows qRT-PCR validation of selected differentially expressed genes in PvSPL4-RNAi transgenic plants SPL4Ri-4 and SPL4Ri-2 compared to WT-NFCX1 revealed by RNA-seq analysis. Genes shown are SAUR1, SAUR9, SAUR14, pectin lyase, expansin A10, expansin B2, expansin B4, YABBY, PvWUS, PvJ24105, GHF 16, and PvWOX4.

To investigate the regulatory mechanisms of PvSPL4, representative SPL4Ri lines with different PvSPL4 expression levels and bud developmental status (FIG. 4) were selected for RNA-seq analysis. A total of 294,015 transcripts were identified by blasting against the Panicum virgatum v1.1 genome sequence (phytozome.jgi.doe.gov/pz/portal.html#!info?alias=Org_Pvirgatum). 68,073 transcripts passed the test and 15,639 were identified with significant differences in various samples. Differential analysis further identified 132 up-regulated genes and 501 down-regulated genes with abundance changing more than twofold in transgenic plants relative to the WT-NFCX1. Nine up-regulated and nine down-regulated genes were selected and subjected to qRT-PCR verification. 94.4% (17 out of 18) of the tested genes showed consistent results with RNA-seq (FIG. 21 and FIG. 22), indicating the high reliability of RNA-seq analysis. Among the 132 up-regulated genes, many genes are involved in carbohydrate and lipid biosynthesis/metabolic processes, indicating that carbohydrates and lipids are needed to supply the necessary molecules and energy for the stable cell division required for axillary bud initiation. Specifically, LAX1 was undetectable in wild type but substantially up-regulated in the node meristems of transgenic plants (FIG. 21A), suggesting LAX1's predominant role in the PvSPL4 regulation pathway. The second highest up-regulated gene is YABBY, which increased over 70- and 50-fold in RNA-seq and qRT-PCR analyses, respectively (FIG. 22). YABBY is a well-known regulator of lateral organ development in many species (Bowman, Curr. Opin. Plant Biol. 3:17-22, 2000; Yamaguchi, et al., Plant Cell 16:500-509, 2004; Lin, et al., Nat. Genet. 44:720-724, 2012; Fourquin, et al., Ann. Bot. 114:1535-1544, 2014), and a recent study indicated that it is essential for the miR165 regulation of leaf primordium development in Arabidopsis (Tatematsu, et al., 2015). The results suggest that YABBY may be involved in PvSPL4 regulation of axillary bud initiation. Similar to LAX1, MOC1 was also significantly up-regulated during bud initiation (FIG. 21A), indicating that both LAX1 and MOC1 are involved in the PvSPL4 regulation pathway.

The down-regulated genes include 11 auxin responsive genes but no auxin biosynthetic gene. LAX1 is known to control auxin transport specifically at the site of axillary meristem initiation in rice (Oikawa and Kyozuka, 2009) and maize (Gallavotti, et al., Plant Physiol. 147:1913-1923, 2008). The present analysis showed that IAA accumulation was dramatically decreased in node axillary meristems but increased in the surrounding tissues of the SPL4Ri plants compared to wild type (FIG. 21B). These results suggest that auxin efflux in the axillary meristems is associated with the up-regulation of LAX1 by PvSPL4 and this auxin export is required for axillary bud formation.

Example 20

A PvSPL4 Ortholog Regulates Branching and Shoot Architecture in Medicago.

Figure 6:
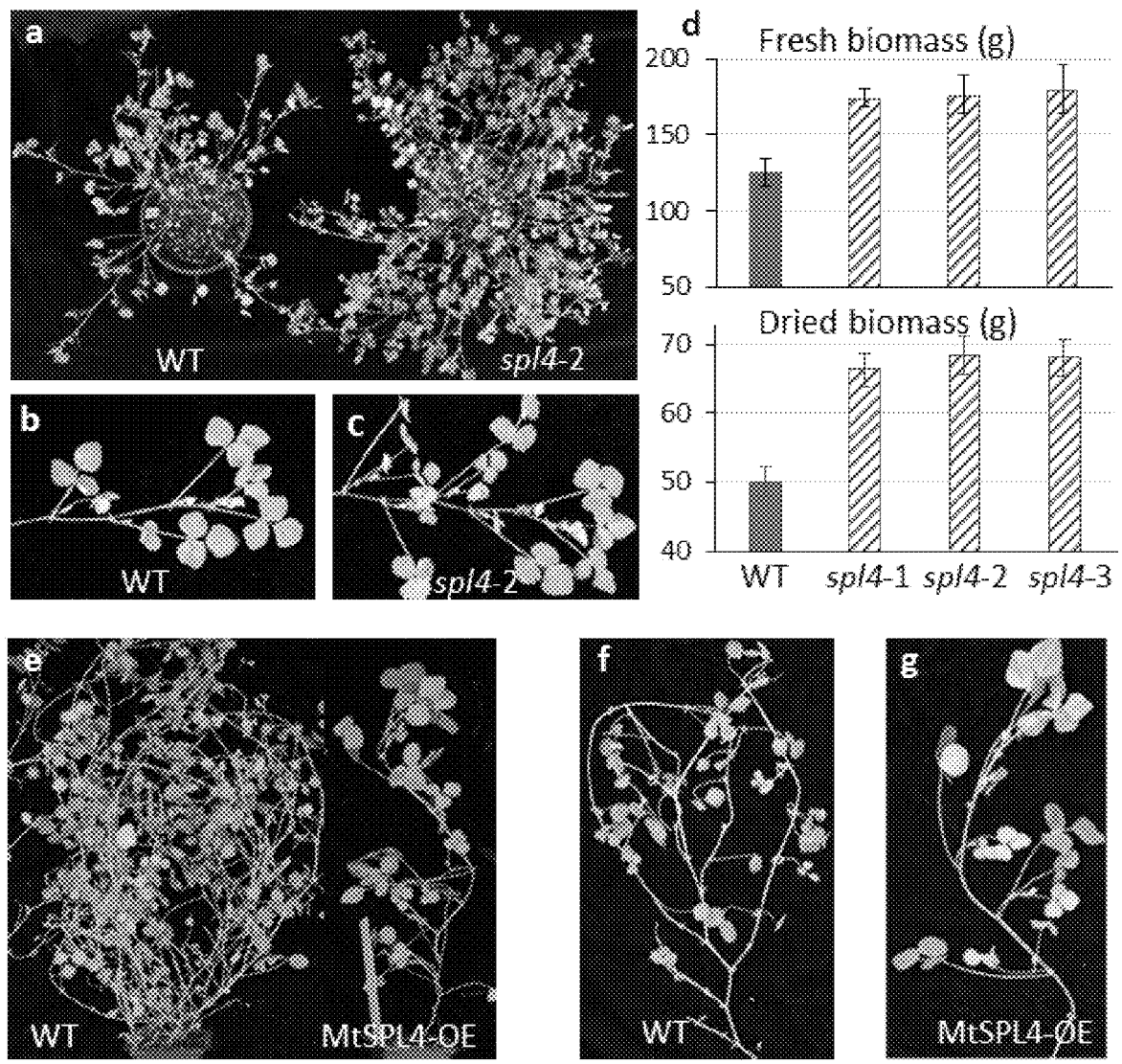
FIG. 6—Panels a-g show phenotype of MtSPL4 knockout mutants and MtSPL4 overexpressing transgenic plants in *Medicago truncatula*.
Figure 23:
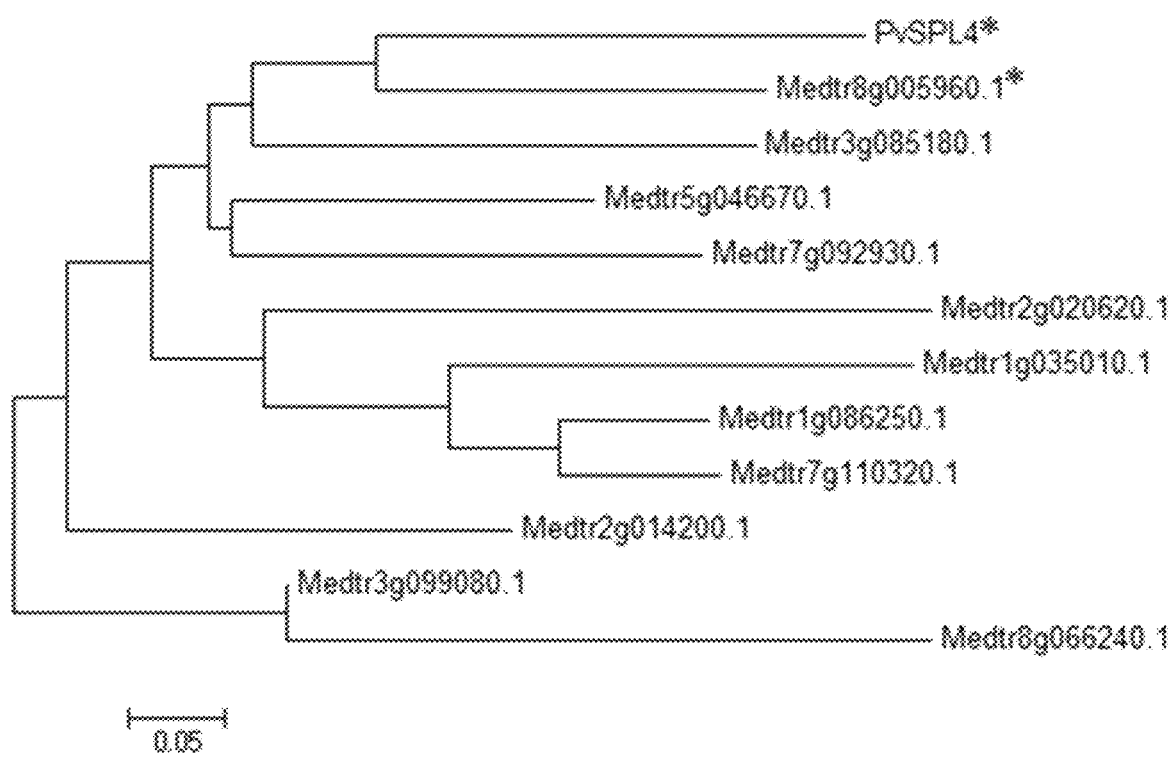
FIG. 23—Shows phylogenetic analysis of PvSPL4 and its ortholog genes in *M. truncatula*.
Figure 25:
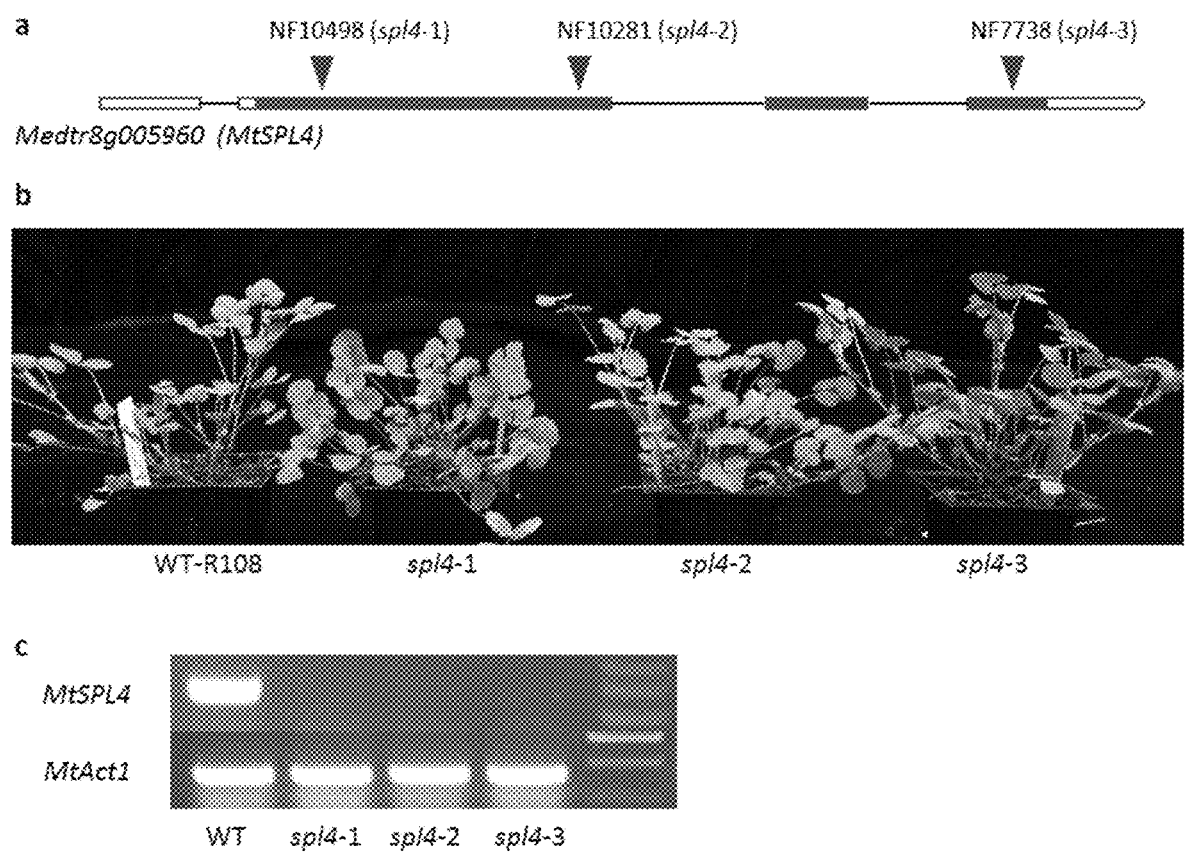
FIG. 25—Panels a-c show three Tnt 1 mutant alleles of MtSPL4 in *M. truncatula*.
Figure 26:
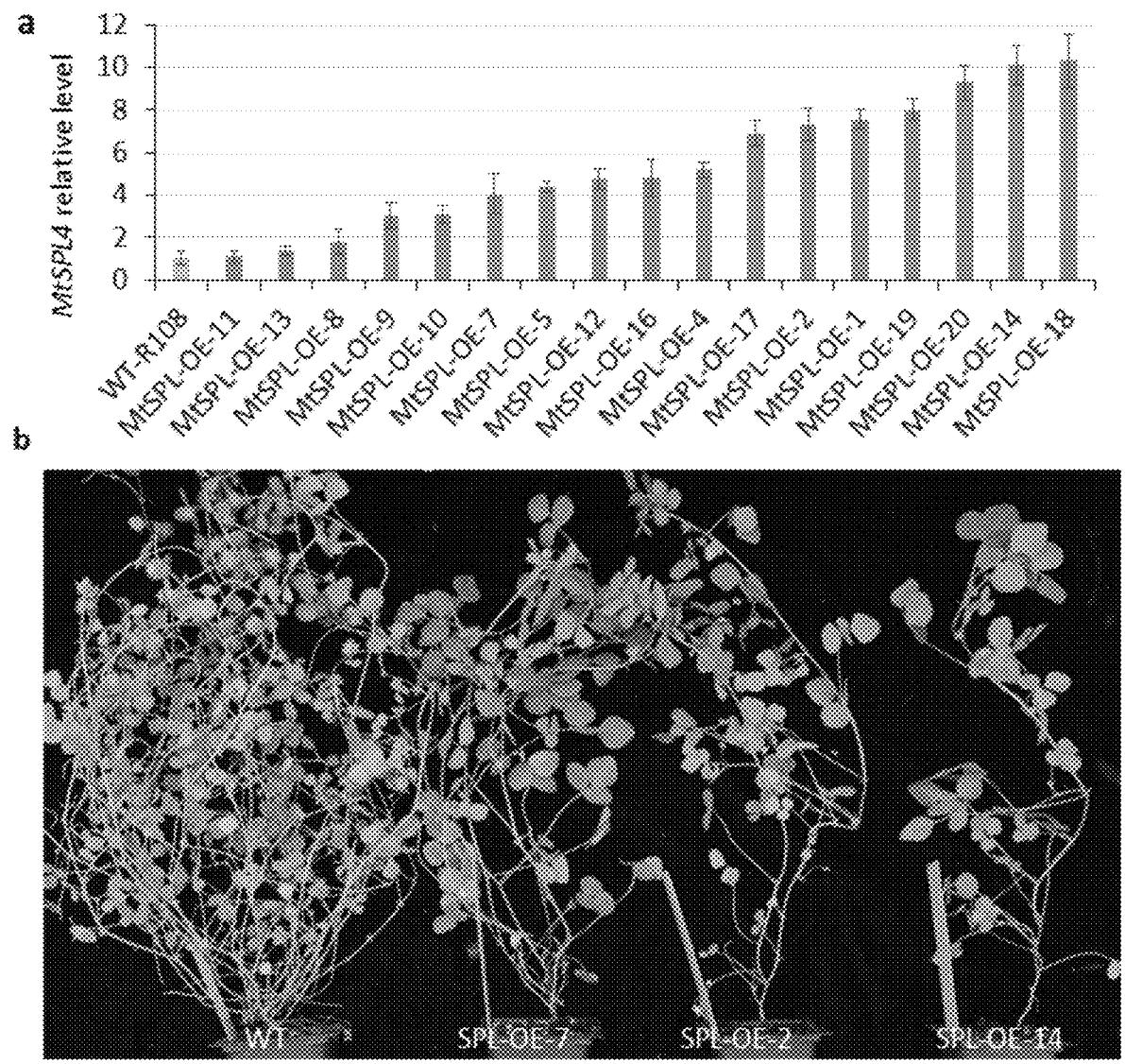
FIG. 26—Panels a and b show characterization of transgenic *M. truncatula* plants overexpressing MtSPL4 compared to WT.
Figure 27:
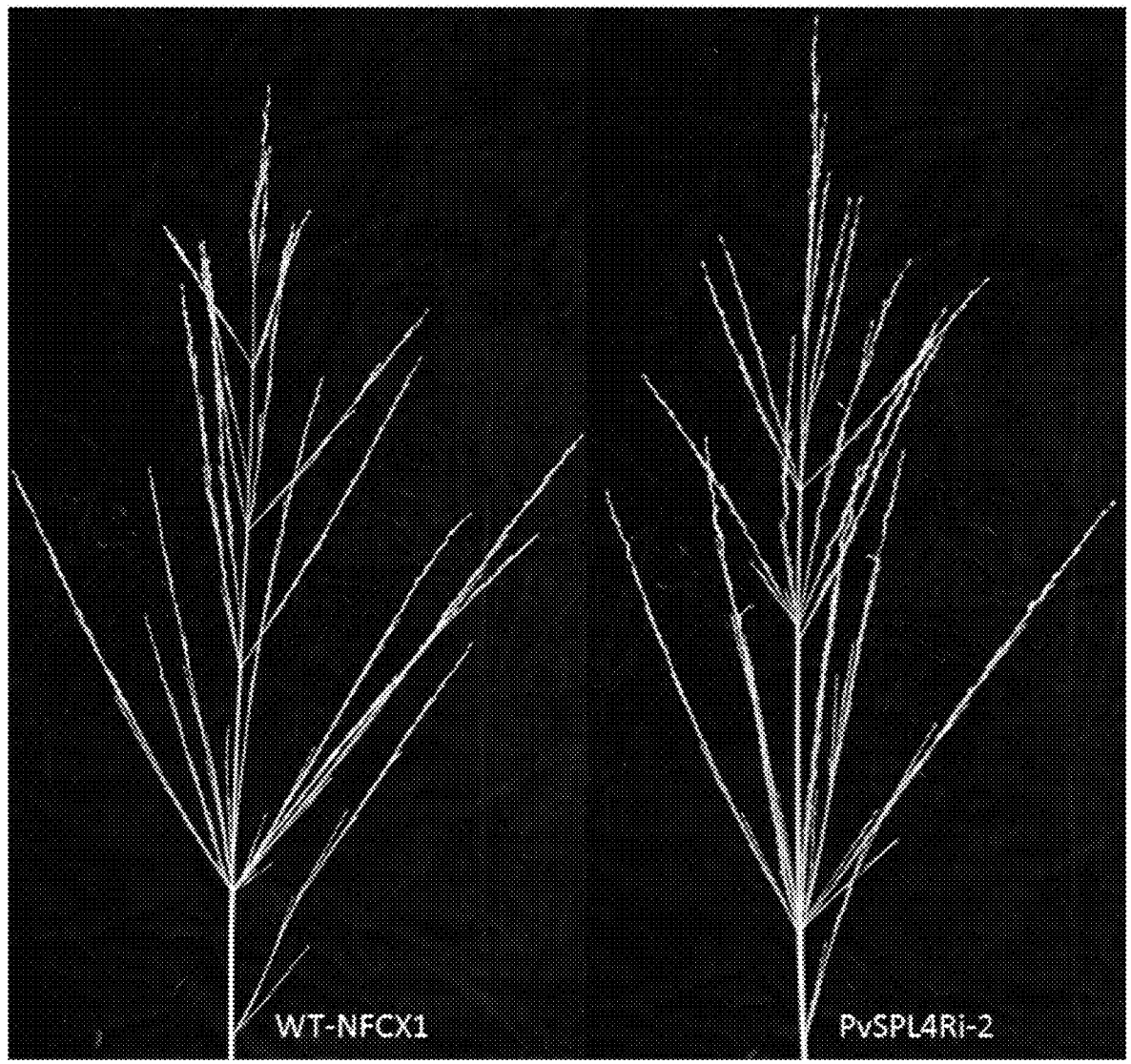
FIG. 27—Shows panicle branches of WT-NFCX1 (left) and corresponding transgenic PvSPL4Ri-2 (right). Knockdown of PvSPL4 does not have apparent impact on panicle branching.

Based on revealed genome wide sequence homology search, 11 SPLs were identified in M. truncatula. Phylogenetic analysis showed that Medtr8g005960 is the closest one to PvSPL4 (FIG. 23). Amino acid sequence analysis that these two proteins share a 75% identity in the SQUAMOSA-promoter binding domains (FIG. 24). Medtr8g005960 was therefore named MtSPL4. Three retrotransposon Tnt1-tagged mutants (spl4-1, 2 and 3) were identified that have insertions in different exons of MtSPL4 (FIG. 25A). Shoot architecture was altered in these mutants (FIG. 6A; FIG. 25B) with a significant increase in branching (FIG. 6B and FIG. 6C). Accordingly, biomass yield was also dramatically increased (FIG. 6D). To further confirm its function, MtSPL4 was overexpressed in M. truncatula wild-type R108 and resulted in decreases in both primary and secondary branch numbers (FIG. 6E-FIG. 6G; FIG. 26). Notably, the transgenic lines with over 10-fold expression increase of MtSPL4 had only a single primary branch (FIG. 6G); thus, shoot architecture was dramatically altered. The results further confirmed that SPL4 directly regulates branching and shoot architecture and that this mechanism is highly conserved in plants. Meanwhile, the miR156-SPL4 module has no significant impact on panicle branching (FIG. 27).

In summary, the present results demonstrate that miR156-SPL4 is a new module regulating axillary bud initiation, particularly the development of aerial buds. This module represents a conserved mechanism that regulates shoot architecture across grass and legume species. Furthermore, genetic manipulation of the module offers an effective approach to enhance biomass productivity of important agricultural and biofuel crops.

What is claimed is:

1. A method of increasing biomass yield or regrowth after cutting in a legume plant, comprising down-regulating SPL4 gene function in said legume plant by mutating the SPL4 gene or by expressing an antisense or RNAi molecule targeting the SPL4 gene function and being complementary to all or a portion of the SPL4 mRNA coding sequence, and identifying a legume plant wherein the regrowth after cutting is increased as compared to a legume plant that lacks said down-regulation of the SPL4 gene function.

2. The method of claim 1, wherein the legume plant is alfalfa.

3. The method of claim 1 further comprising
   (a) obtaining the legume plant comprising down-regulation of SPL4 gene function;
   (b) growing said legume plant;
   (c) crossing said legume plant with itself or another distinct plant to produce progeny plants; and
   (d) selecting a progeny plant comprising down-regulation of SPL4 gene function, wherein said progeny plant comprises increased regrowth after cutting as compared to a plant that lacks said down-regulation.

4. A transgenic legume plant produced by the method of claim 3.

5. The transgenic plant of claim 4, further defined as alfalfa.

6. The transgenic plant of claim 4, further defined as an $R_0$ transgenic plant.

7. The transgenic plant of claim 4, further defined as a progeny plant of any generation of an $R_0$ transgenic plant, wherein the transgenic plant has inherited a recombinant DNA molecule from the $R_0$ transgenic plant.

8. The method of claim 1, wherein the SPL4 coding sequence has at least 90% sequence identity to SEQ ID NO:1, 6, or 9.

9. The method of claim 8, wherein the SPL4 coding sequence has at least 95% sequence identity to SEQ ID NO:1, 6, or 9.

10. The method of claim 9, wherein the SPL4 coding sequence is SEQ ID NO:1, 6, or 9.

11. The method of claim 8, wherein the SPL4 coding sequence has at least 90% sequence identity to SEQ ID NO: 1.

12. The method of claim 8, wherein the SPL4 coding sequence has at least 90% sequence identity to SEQ ID NO: 6.

13. The method of claim 8, wherein the SPL4 coding sequence has at least 90% sequence identity to SEQ ID NO: 9.

14. The method of claim 9, wherein the SPL4 coding sequence has at least 95% sequence identity to SEQ ID NO: 1.

15. The method of claim 9, wherein the SPL4 coding sequence has at least 95% sequence identity to SEQ ID NO: 6.

16. The method of claim 9, wherein the SPL4 coding sequence has at least 95% sequence identity to SEQ ID NO: 9.

17. The method of claim 10, wherein the SPL4 coding sequence is SEQ ID NO: 1.

18. The method of claim 10, wherein the SPL4 coding sequence is SEQ ID NO: 6.

19. The method of claim 10, wherein the SPL4 coding sequence is SEQ ID NO: 9.

* * * * *

UNITED STATES PATENT AND TRADEMARK OFFICE
CERTIFICATE OF CORRECTION

| | |
|---|---|
| PATENT NO. | : 11,193,134 B2 |
| APPLICATION NO. | : 16/029367 |
| DATED | : December 7, 2021 |
| INVENTOR(S) | : Jiqing Gou and Zeng-Yu Wang |

It is certified that error appears in the above-identified patent and that said Letters Patent is hereby corrected as shown below:

On the Title Page

Please insert the Assignee: --NOBLE RESEARCH INSTITUTE, LLC, ARDMORE, OK--

Signed and Sealed this
Twenty-sixth Day of December, 2023

Katherine Kelly Vidal
*Director of the United States Patent and Trademark Office*

SEQUENCE LISTING

```
<160> NUMBER OF SEQ ID NOS: 19

<210> SEQ ID NO 1
<211> LENGTH: 984
<212> TYPE: DNA
<213> ORGANISM: Medicago truncatula

<400> SEQUENCE: 1
atgttggact atgaatgggg taacccatca aacatcatgc ttaccggaaa tgaagacaac      60
tccggtgcag cagccaccga tcaagcccac cgtcaaatct tcgaccacta tgcttctcaa     120
gctatgttat ccgacaacta ccttaacgga cctggtggtg gacccaccat cgacataaac     180
agtggtgatt ttactcatca ccacaaccag tttagcccac acaaccagca gcaccataat     240
```

```
atccatcagt ccttcttcga cccacgggct tttcatggag ggtcatcaac tgcttcttct      300
taccctccac ctcaaccaca acctcctcct tccatgctct cccttgaccc tcttcctggt      360
catggacata gccctggatt cctcctcgta ccaaaatccg aggatgttaa cagacccatt      420
gacttcgtgg gctctagact tggactcaac cttggtggcc gcacttactt ctcttccgaa      480
gatgacttcg tgacccgcct ttaccgtcgg tctagaccac ctgaaccggg ttccacaggt      540
tcttcgaact cacctaggtg tcaagccgaa ggttgcaatg ctgatctatc tcaggctaag      600
cattaccacc gccgccacaa agtttgtgag tttcactcga aggcagccac cgtcgttgca      660
gctgggttga ctcagcggtt ctgccagcaa tgcagcaggt tccatcttct atctgagttt      720
gataatggaa aacgtagctg caggaagaga ttggctgatc ataatcgtcg taggagaaaa      780
actcagcacc ctaatactca agatattcac aaatctcaca atactttgga tagttctgcc      840
acaagatccc ctccggagtc tggaactcaa tccacatctt ctgtgactgt ggccgtatct      900
ccaccggatt attttcgaca aaggtcgtac caaaccccaa gcccttcaac aacttcaagc      960
tcaatgtttt tctccaccgg gtag                                            984
```

<210> SEQ ID NO 2
<211> LENGTH: 327
<212> TYPE: PRT
<213> ORGANISM: Medicago truncatula

<400> SEQUENCE: 2

```
Met Leu Asp Tyr Glu Trp Gly Asn Pro Ser Asn Ile Met Leu Thr Gly
1               5                   10                  15

Asn Glu Asp Asn Ser Gly Ala Ala Ala Thr Asp Gln Ala His Arg Gln
                20                  25                  30

Ile Phe Asp His Tyr Ala Ser Gln Ala Met Leu Ser Asp Asn Tyr Leu
            35                  40                  45

Asn Gly Pro Gly Gly Gly Pro Thr Ile Asp Ile Asn Ser Gly Asp Phe
        50                  55                  60

Thr His His His Asn Gln Phe Ser Pro His Asn Gln Gln His His Asn
65                  70                  75                  80

Ile His Gln Ser Phe Phe Asp Pro Arg Ala Phe His Gly Gly Ser Ser
                85                  90                  95

Thr Ala Ser Ser Tyr Pro Pro Pro Gln Pro Gln Pro Pro Pro Ser Met
                100                 105                 110

Leu Ser Leu Asp Pro Leu Pro Gly His Gly His Ser Pro Gly Phe Leu
            115                 120                 125

Leu Val Pro Lys Ser Glu Asp Val Asn Arg Pro Ile Asp Phe Val Gly
        130                 135                 140

Ser Arg Leu Gly Leu Asn Leu Gly Gly Arg Thr Tyr Phe Ser Ser Glu
145                 150                 155                 160

Asp Asp Phe Val Thr Arg Leu Tyr Arg Arg Ser Arg Pro Pro Glu Pro
                165                 170                 175

Gly Ser Thr Gly Ser Ser Asn Ser Pro Arg Cys Gln Ala Glu Gly Cys
            180                 185                 190

Asn Ala Asp Leu Ser Gln Ala Lys His Tyr His Arg His Lys Val
        195                 200                 205

Cys Glu Phe His Ser Lys Ala Ala Thr Val Val Ala Ala Gly Leu Thr
            210                 215                 220

Gln Arg Phe Cys Gln Gln Cys Ser Arg Phe His Leu Leu Ser Glu Phe
225                 230                 235                 240
```

Asp Asn Gly Lys Arg Ser Cys Arg Lys Arg Leu Ala Asp His Asn Arg
            245                 250                 255

Arg Arg Arg Lys Thr Gln His Pro Asn Thr Gln Asp Ile His Lys Ser
        260                 265                 270

His Asn Thr Leu Asp Ser Ser Ala Thr Arg Ser Pro Pro Glu Ser Gly
        275                 280                 285

Thr Gln Ser Thr Ser Ser Val Thr Val Ala Val Ser Pro Pro Asp Tyr
    290                 295                 300

Phe Arg Gln Arg Ser Tyr Gln Thr Pro Ser Pro Ser Thr Thr Ser Ser
305                 310                 315                 320

Ser Met Phe Phe Ser Thr Gly
            325

<210> SEQ ID NO 3
<211> LENGTH: 500
<212> TYPE: DNA
<213> ORGANISM: Medicago truncatula

<400> SEQUENCE: 3
aaaatacaaa attgaatttt ctattgtaac atcaagacat tgtatcagat caaaacgact        60
aagatttatt gcaatgtaaa actgtgtgaa ctagctttgg tggagaaccc taacccttaa       120
catactagtg tttgttattt gtctaataaa aaaatgtgt ggtgtaaaat taaaattgaa        180
aaacaataaa atgaaacaaa aaatttacac ttaggtgaaa aggtaatttc cattggaagc       240
atatccagag tacagatcac ccaccaatta cccactgtct gcagaagccg cctcataagc       300
tgaatttccc tcaaactcac acaaacttaa ctcaactaga gagagagaga gagaatgaga       360
attgagttac aagagtaact ttcctattgg tagagagaga tgaggagatg agacaaaag        420 tgttcagctt ttttagggtg aaagtgagat ctttttaagcg cacaacccat ttagcatagc      480
agaaacaaag aaagaaagaa                                                  500

<210> SEQ ID NO 4
<211> LENGTH: 525
<212> TYPE: DNA
<213> ORGANISM: Arabidopsis thaliana

<400> SEQUENCE: 4
atggagggta agagatcaca aggacaaggt tacatgaaaa agaagtctta ccttgtggaa        60
gaagatatgg agactgatac ggatgaagaa gaggaagtag gtagggatag agttagaggg       120
tctagaggta gcatcaatcg tggtggctcg ttgcggcttt gccaagtaga tagatgcaca       180
gctgatatga agaggcaaaa actgtatcac cggagacaca agtgtgtga agttcatgca        240 aaggcatctt ctgtctttct ctcaggactt aaccaacgct tttgtcaaca atgcagtagg       300
tttcatgacc tccaagagtt tgatgaagct aagagaagtt gcaggaggcg cttagctgga       360
cacaatgagc gaagaaggaa gagctctggt gagagtactt atggagaagg atcaggtcgg       420
agaggaatca atggtcaggt ggtgatgcag aatcaagaaa gatcaagggt agagatgaca       480
cttcctatgc caaactcatc attcaagcga ccacagatta gatag                      525

<210> SEQ ID NO 5
<211> LENGTH: 174
<212> TYPE: PRT
<213> ORGANISM: Arabidopsis thaliana

<400> SEQUENCE: 5

```
Met Glu Gly Lys Arg Ser Gln Gly Gln Gly Tyr Met Lys Lys Ser
1               5                   10                  15

Tyr Leu Val Glu Glu Asp Met Glu Thr Asp Thr Asp Glu Glu Glu
            20                  25                  30

Val Gly Arg Asp Arg Val Arg Gly Ser Arg Gly Ser Ile Asn Arg Gly
                35                  40                  45

Gly Ser Leu Arg Leu Cys Gln Val Asp Arg Cys Thr Ala Asp Met Lys
    50                  55                  60

Glu Ala Lys Leu Tyr His Arg Arg His Lys Val Cys Glu Val His Ala
65                  70                  75                  80

Lys Ala Ser Ser Val Phe Leu Ser Gly Leu Asn Gln Arg Phe Cys Gln
                85                  90                  95

Gln Cys Ser Arg Phe His Asp Leu Gln Glu Phe Asp Glu Ala Lys Arg
                100                 105                 110

Ser Cys Arg Arg Arg Leu Ala Gly His Asn Glu Arg Arg Lys Ser
                115                 120                 125

Ser Gly Glu Ser Thr Tyr Gly Gly Ser Gly Arg Arg Gly Ile Asn
        130                 135                 140

Gly Gln Val Val Met Gln Asn Gln Glu Arg Ser Arg Val Glu Met Thr
145                 150                 155                 160

Leu Pro Met Pro Asn Ser Ser Phe Lys Arg Pro Gln Ile Arg
                165                 170

<210> SEQ ID NO 6
<211> LENGTH: 477
<212> TYPE: DNA
<213> ORGANISM: Glycine max

<400> SEQUENCE: 6
atggtggtga ggagtgacag gttgaagagg gatgtggcag attgtggtga caacaaccaa      60
aacgggtacg tggagcaaga gaagaagata aaagggtgc atatatgcgg tgttgtcaac      120
gccgatcttc atgaggccaa gcagtaccac aggaggcaca gggtgtgtga gtatcatgta     180
aaggctcagg ttgtgcttgt tgatgaggtt agacaacggt tctgtcagca atgtagcaga     240
ttccacgaat tagctgaatt tgatgacaca aaaagaagtt gccgcagcag tttggccgga     300
cacaatgaac ggaggagaaa gaactcagat cagtctcaag cagaagggtc aagccgcaac     360
aaagggacag ggcaccctca attgaaggac attacttgtg gtcaggctga tgagagggg      420 agaattcaga taacaatcca cgaaaatgct gcttacaaac atttccagat aagatga        477

<210> SEQ ID NO 7
<211> LENGTH: 158
<212> TYPE: PRT
<213> ORGANISM: Glycine max

<400> SEQUENCE: 7

Met Val Val Arg Ser Asp Arg Leu Lys Arg Asp Val Ala Asp Cys Gly
1               5                   10                  15

Asp Asn Asn Gln Asn Gly Tyr Val Glu Gln Glu Lys Lys Ile Lys Gly
            20                  25                  30

Val His Ile Cys Gly Val Val Asn Ala Asp Leu His Glu Ala Lys Gln
        35                  40                  45

Tyr His Arg Arg His Arg Val Cys Glu Tyr His Val Lys Ala Gln Val
    50                  55                  60

Val Leu Val Asp Glu Val Arg Gln Arg Phe Cys Gln Gln Cys Ser Arg
65                  70                  75                  80
```

Phe His Glu Leu Ala Glu Phe Asp Asp Thr Lys Arg Ser Cys Arg Ser
                85                  90                  95

Ser Leu Ala Gly His Asn Glu Arg Arg Arg Lys Asn Ser Asp Gln Ser
            100                 105                 110

Gln Ala Glu Gly Ser Ser Arg Asn Lys Gly Thr Gly His Pro Gln Leu
        115                 120                 125

Lys Asp Ile Thr Cys Gly Gln Ala Asp Glu Arg Gly Arg Ile Gln Ile
    130                 135                 140

Thr Ile His Glu Asn Ala Ala Tyr Lys His Phe Gln Ile Arg
145                 150                 155

<210> SEQ ID NO 8
<211> LENGTH: 500
<212> TYPE: DNA
<213> ORGANISM: Glycine max

<400> SEQUENCE: 8
tattcaaata taaatcatat tattttaata tcaattttaa tctgagatct attcacacat      60
tctaggaaag tgtacaagaa tcattttca aacattttaa catgagaaga cttatttatt     120
tactgagagg acctggtcag cctcagtgat ccacacacgc acatcatctt ctactcttcc    180
tcccctcctg cacaactgt cacggtcaca ccacttgatt tcacggtaca cgtagagaag     240
agtcattgtt tgagtctcac tttcacaccc ctcgtcaccg tcttctctag tcccatgtac    300
caccactaca acacacacaa aaaaaaagt cattaagaga ggtggcgaga aaatatggga     360
gcactttgtt gtggtcctta ctctctctca cttttccgcc tttatatata attcctttgt    420
tatcaccacc ctcaaactca gcttcttcaa acttgcaagt tgcaaccatt aattctttca    480
tggaggggtt ggggtcaaag                                                500

<210> SEQ ID NO 9
<211> LENGTH: 510
<212> TYPE: DNA
<213> ORGANISM: Phaseolus vulgaris

<400> SEQUENCE: 9 atggagggt tgaagagggg tgtggtagat tgtggtgaaa accaaaaagg gtacgtggag      60
cttccgcagg agaggaagaa gagagaggg gaggaaggga agaaggagg tgctggtatt     120 ggcatgctgt gttgtcaagc ggagaagtgc aacgcggatc tgcatgaggc taagcaatac    180
cacaggaggc acaaggtgtg tgagtgtcac gccaaggctc aggttgtgct tgttcatggc    240
atcaaacaac ggttctgtca gcaatgtagc agattccacg agctgtctga atttgatgac    300
gcaaaaagaa gttgtcgcag gcgtttggct gtacacaatg aacggaggag aaagaactct    360
tctgatcaat ctcaagcaga agggtcaagc acaaagggt cagaggcccc tcaactgaag     420
gacattgctt gtgttcaggc taatgaaagg ggaagaactc atataacgat acaacaaat    480 tcaccttaca aaatttccaa ataagataa                                      510

<210> SEQ ID NO 10
<211> LENGTH: 169
<212> TYPE: PRT
<213> ORGANISM: Phaseolus vulgaris

<400> SEQUENCE: 10

Met Glu Gly Leu Lys Arg Gly Val Val Asp Cys Gly Glu Asn Gln Lys
1               5                   10                  15

```
Gly Tyr Val Glu Leu Pro Gln Glu Arg Lys Lys Arg Gly Glu
             20                  25                  30
Gly Lys Lys Gly Ala Gly Ile Gly Met Leu Cys Cys Gln Ala Glu
         35                  40                  45
Lys Cys Asn Ala Asp Leu His Glu Ala Lys Gln Tyr His Arg Arg His
 50                  55                  60
Lys Val Cys Glu Cys His Ala Lys Ala Gln Val Val Leu Val His Gly
 65                  70                  75                  80
Ile Lys Gln Arg Phe Cys Gln Gln Cys Ser Arg Phe His Glu Leu Ser
                 85                  90                  95
Glu Phe Asp Asp Ala Lys Arg Ser Cys Arg Arg Leu Ala Val His
                100                 105                 110
Asn Glu Arg Arg Arg Lys Asn Ser Ser Asp Gln Ser Gln Ala Glu Gly
                115                 120                 125
Ser Ser His Lys Gly Ser Glu Ala Pro Gln Leu Lys Asp Ile Ala Cys
            130                 135                 140
Val Gln Ala Asn Glu Arg Gly Arg Thr His Ile Thr Ile Gln Gln Asn
145                 150                 155                 160
Ser Pro Tyr Lys Asn Phe Gln Ile Arg
                165
```

<210> SEQ ID NO 11
<211> LENGTH: 500
<212> TYPE: DNA
<213> ORGANISM: Phaseolus vulgaris

<400> SEQUENCE: 11

```
tctaatttgc aaatttctaa tagagataaa ttatatatct gtttgccatc tataaataat    60
acatgtgcat cttcacttct tataccgtaa ttgcgttttt atagcattat tattcctgtg   120
atatcttgaa tagtacatgt acactctcaa ctacaaatac tcattcaaca cctatcacta   180
tcattatatc tctttctttt cgtgagagaa aaaatattg tctttccagt gtaacataac    240
atgtgttcat tgatatctca ttattcatat atatatatgg aaaaagttt gtttacatat    300
atatgcatat acataatgca gttgaaagaa gattttaacg tgagaatgag aagacttatt   360
tattttagtg acaggacatg ttgaggctca gtgaaccaca caagaacatc atcgtctatt   420
cttcagtcac aactgtcacg gtcccgccac tttaccacaa ttctcccact ccatctcctt   480
cattcaatga ttcaacttgg                                              500
```

<210> SEQ ID NO 12
<211> LENGTH: 192
<212> TYPE: DNA
<213> ORGANISM: Phaseolus vulgaris

<400> SEQUENCE: 12

```
agcgtgctct ctctcttctg tcaaacaatt cagctggtgc tggcaacaac cacccgacca    60
ctcagccgca cctggcctg agcaccctcg ccagcacctc caacgcagtg atgcaagctt    120
catcacaagg gctctggcaa gacggcacag cgcttgatct tcatgcgcgg tttcaggctc   180
tcgatcccct gg                                                      192
```

<210> SEQ ID NO 13
<211> LENGTH: 192
<212> TYPE: DNA
<213> ORGANISM: Phaseolus vulgaris

<400> SEQUENCE: 13

```
cgggtggatg tcttgcagga gtccccgctg actctagctg tgctctctct cttctgtcaa      60
ctcagccatg ggatactacc caaagcgctg gccacagccg tgctgcgtca atgcctgcaa     120
cagcgggctt tgatggcaac cctgtggcac cctccctcat ggcgagtagc tacattgcgt     180
cgagcccctg ga                                                         192

<210> SEQ ID NO 14
<211> LENGTH: 192
<212> TYPE: DNA
<213> ORGANISM: Phaseolus vulgaris

<400> SEQUENCE: 14
ttgactctag ctgtgctctc tctcttctgt caactcagcc atgggatact acccaaagcg      60
ctggccacag ccgtgctgcg tcaatgcctg caacagcggg ctttgatggc aaccctgtgg     120
caccctccct catggcgagt agctacattg cgtcgagccc ctggactggc tctcagggcc     180
actcaggcgg gc                                                         192

<210> SEQ ID NO 15
<211> LENGTH: 21
<212> TYPE: RNA
<213> ORGANISM: Artificial sequence
<220> FEATURE:
<223> OTHER INFORMATION: micro RNA 156

<400> SEQUENCE: 15
acugucuucu cucucucgug u                                                21

<210> SEQ ID NO 16
<211> LENGTH: 1133
<212> TYPE: DNA
<213> ORGANISM: Phaseolus vulgaris

<400> SEQUENCE: 16
caagacctac cactgccgcc acaaggtgtg cgccatgcac tccaaggctc cccttgtcgt      60
cgtcaacggc atggaacaac gcattctgcc agcagtgcag caggttccac cagttgcatg     120
aatttgacca caaaaacgc agctgccgta gacgccttac aggccacaat gaacgccgga     180
ggaggccgcc tgctggacct tttgcatcac gctatggtcg ctttgctgca tccttgggcg     240
gagagcctgg caggttcaga agcttttctgt tggatttcac atacccaagg gttccaagca     300
gcatgaggga tgggtggcag gcggttcgtc ctggggaaag ggtgcctgat agtatccagt     360
ggcaagcaag cttagatcct catcatcaca gtgcaatcgc aggatatgtg tgcccactca     420
tatggcagcc agggtagcgc ctcatcaggg ccaccggtgt tccccgggcc ggagctccct     480
ccgggtggat gtcttgcagg agtccccgct gactctagct gtgctctctc tcttctgtca     540
actcagccat gggatactac ccaaagcgct ggccacagcc gtgctgcgtc aatgcctgca     600
acagcgggct tgatggcaa ccctgtggca ccctccctca tggcgagtag ctacattgcg     660
tcgagcccct ggactggctc tcagggccac tcaggcgggc gcaacgtgac acctcagttg     720
ccacctgaag tcccctcga tgaggtgcat tctggctcta gcagctatca tggccggttc     780
tcaggtgagc tcgagcttgc cctgcaggga acaggccag tgccagcgcc gcgcatcgat     840
cagggctcca caagcacatt cgaccaggcc agcaacacat cggactggtc gctctaggag     900
gccaaataaa ccaccaccga gatcatagtc gctcggagag atggaactga tgaaagcctg     960
atgctgcatg cggtttgcta gcttcaagct tccagtatga tatgtaagaa accctgtaa    1020
```

```
tgtcaggcga ctaatttctt tttgtggttg tccatgaact catctgttgc gtcatgtaga    1080
cctccatgat ttgaagttat cagtatgctt atcgatgact cgttgtttaa aaa           1133

<210> SEQ ID NO 17
<211> LENGTH: 1201
<212> TYPE: DNA
<213> ORGANISM: Phaseolus vulgaris

<400> SEQUENCE: 17
gaactaaata atttgtccta aatttggtcg gaggtacaag gagtagtatc tatttgcact      60
tagactttga gatctggata ttgcaacttg tatgctccct gttcctcacc ctttaaattt     120
atatataaaa aagaagcttg aatcatcatt tctctattca cataaactgc aggttccacc     180
agttgcatga atttgaccaa caaaaacgca gctgccgtag acgccttaca ggccacaatg     240
aacgccggag gaggccgcct gctggacctt ttgcatcacg ctatggtcgc tttgctgcat     300
ccttgggcgg agagcctggc aggttcagaa gctttctgtt ggatttcaca tacccaaggg     360
ttccaagcag catgagggat gggtggcagg cggttcgtcc tggggaaagg gtgcctgata     420
gtatccagtg gcaagcaagc ttagatcctc atcatcacag tgcaatcgca ggatatgtgt     480
gcccactcat atggcagcca gggtagcgcc tcatcagggc caccggtgtt ccccgggccg     540
gagctccctc cgggtggatg tcttgcagga gtccccgttg actctagctg tgctctctct     600
cttctgtcaa ctcagccatg gatactacc caaagcgctg ccacagccg tgctgcgtca      660 atgcctgcaa cagcgggctt tgatggcaac cctgtggcac cctccctcat ggcgagtagc     720
tacattgcgt cgagcccctg gactggctct cagggccact caggcgggcg caacgtgaca     780
cctcagttgc cacctgaagt cccctcgat gaggtgcatt ctggctatag cagccatcat      840
ggccagttct caggtgagct cgagcttgcc ctgcagggaa acaggcctgc gccagcgccg     900
cgcatcgatc agggctccac aagcacattc gaccaggcca gcaacacatc ggactggtcg     960
ctctaggagg ccaaataaac caccaccgag atcatagtcg ctcggagaga tggaactgat    1020
gaaagcctga tgctgcatgc ggtttgctag cgtcaaactt ccagtatgat atgtaagaaa    1080
cccctgcaat gtcaggcgac taatttcttt tgtggttgtc catgaactca tctgttgtgt    1140
catgtagacc tccatgattt gaagttatca gtatgcttat cgatgactcg ttgttttaaaa    1200 a                                                                    1201

<210> SEQ ID NO 18
<211> LENGTH: 307
<212> TYPE: PRT
<213> ORGANISM: Phaseolus vulgaris

<400> SEQUENCE: 18

Met Glu Ala Ala Ser Ala Gly Gly Ser Gly Gly Gly Gly Asp Asp
1               5                   10                  15

His Leu His Gly Leu Lys Phe Gly Lys Lys Ile Tyr Phe Glu Asp Ala
                20                  25                  30

Gly Ala Ser Gly Ser Gly Ser Gly Ser Ser Gly Gly Ser Ala Ser Gly
            35                  40                  45

Ala Ser Glu Pro Leu Pro Pro Pro Ser Ala Ser Pro Pro Arg Ala Ala
        50                  55                  60

Ala Gly Arg Arg Gly Arg Gly Ala Ala Gly Gly Ala Ala Gly Ser Ser
65                  70                  75                  80

Ala Pro Pro Arg Cys Gln Val Glu Gly Cys Asn Val Asp Leu Thr Gly
                85                  90                  95
```

```
Ala Lys Thr Tyr His Cys Arg His Lys Val Cys Ala Met His Ser Lys
                100                 105                 110

Ala Pro Leu Val Val Asn Gly Ile Glu Gln Arg Phe Cys Gln Gln
            115                 120                 125

Cys Ser Arg Phe His Gln Leu His Glu Phe Asp Gln Gln Lys Arg Ser
130                 135                 140

Cys Arg Arg Arg Leu Met Gly His Asn Glu Arg Arg Arg Pro Pro
145                 150                 155                 160

Ala Gly Pro Leu Ala Ser Arg Tyr Gly Arg Leu Ala Ala Ser Leu Gly
                165                 170                 175

Gly Glu Pro Gly Arg Phe Arg Ser Phe Leu Leu Asp Phe Ser Tyr Pro
            180                 185                 190

Arg Val Pro Ser Ser Met Arg Asp Gly Trp Gln Ala Ala Gln Pro Gly
            195                 200                 205

Glu Arg Val Pro Gly Ser Met Gln Trp Gln Ser Ser Leu Asp Pro His
            210                 215                 220

His His Ser Ala Ile Ala Gly Tyr Gly Ala His Ser Tyr Gly Ser Gln
225                 230                 235                 240

Gly Ser Pro Ser Ser Gly Pro Pro Val Phe Pro Gly Pro Glu Leu Pro
                245                 250                 255

Pro Gly Gly Cys Leu Ala Gly Val Pro Ala Asp Ser Ser Cys Ala Leu
            260                 265                 270

Ser Leu Leu Ser Thr Gln Pro Trp Asp Thr Thr Gln Ser Ala Gly His
                275                 280                 285

Ser Arg Ala Ala Ser Met Pro Ala Thr Ala Gly Phe Asp Gly Asn Pro
            290                 295                 300

Val Ala Pro
305

<210> SEQ ID NO 19
<211> LENGTH: 327
<212> TYPE: PRT
<213> ORGANISM: Medicago truncatula

<400> SEQUENCE: 19

Met Leu Asp Tyr Glu Trp Gly Asn Pro Ser Asn Ile Met Leu Thr Gly
1               5                   10                  15

Asn Glu Asp Asn Ser Gly Ala Ala Ala Thr Asp Gln Ala His Arg Gln
            20                  25                  30

Ile Phe Asp His Tyr Ala Ser Gln Ala Met Leu Ser Asp Asn Tyr Leu
        35                  40                  45

Asn Gly Pro Gly Gly Gly Pro Thr Ile Asp Ile Asn Ser Gly Asp Phe
    50                  55                  60

Thr His His His Asn Gln Phe Ser Pro His Asn Gln His Asn
65                  70                  75                  80

Ile His Gln Ser Phe Phe Asp Pro Arg Ala Phe His Gly Gly Ser Ser
                85                  90                  95

Thr Ala Ser Ser Tyr Pro Pro Pro Gln Pro Gln Pro Pro Ser Met
            100                 105                 110

Leu Ser Leu Asp Pro Leu Pro Gly His Gly His Ser Pro Gly Phe Leu
        115                 120                 125

Leu Val Pro Lys Ser Glu Asp Val Asn Arg Pro Ile Asp Phe Val Gly
    130                 135                 140

Ser Arg Leu Gly Leu Asn Leu Gly Gly Arg Thr Tyr Phe Ser Ser Glu
```

-continued

```
        145                 150                 155                 160
Asp Asp Phe Val Thr Arg Leu Tyr Arg Arg Ser Arg Pro Pro Glu Pro
                    165                 170                 175

Gly Ser Thr Gly Ser Ser Asn Ser Pro Arg Cys Gln Ala Glu Gly Cys
                180                 185                 190

Asn Ala Asp Leu Ser Gln Ala Lys His Tyr His Arg Arg His Lys Val
            195                 200                 205

Cys Glu Phe His Ser Lys Ala Ala Thr Val Val Ala Ala Gly Leu Thr
        210                 215                 220

Gln Arg Phe Cys Gln Gln Cys Ser Arg Phe His Leu Leu Ser Glu Phe
225                 230                 235                 240

Asp Asn Gly Lys Arg Ser Cys Arg Lys Arg Leu Ala Asp His Asn Arg
                245                 250                 255

Arg Arg Arg Lys Thr Gln His Pro Asn Thr Gln Asp Ile His Lys Ser
                260                 265                 270

His Asn Thr Leu Asp Ser Ser Ala Thr Arg Ser Pro Pro Glu Ser Gly
            275                 280                 285

Thr Gln Ser Thr Ser Ser Val Thr Val Ala Val Ser Pro Pro Asp Tyr
        290                 295                 300

Phe Arg Gln Arg Ser Tyr Gln Thr Pro Ser Pro Ser Thr Thr Ser Ser
305                 310                 315                 320

Ser Met Phe Phe Ser Thr Gly
                325
```